US005358936A

United States Patent [19]

Gordon et al.

[11] Patent Number: 5,358,936

[45] Date of Patent: * Oct. 25, 1994

[54] ANIONIC FURANOSE DERIVATIVES, METHODS OF MAKING AND USING THE SAME

[75] Inventors: Paul Gordon, 1220 E. 48th St., Chicago, Ill. 60615; Edward P. Gamson, Highland Park, Ill.

[73] Assignee: Paul Gordon, Chicago, Ill.

[ * ] Notice: The portion of the term of this patent subsequent to Mar. 10, 2009 has been disclaimed.

[21] Appl. No.: 738,597

[22] Filed: Jul. 31, 1991

Related U.S. Application Data

[63] Continuation-in-part of Ser. No. 563,103, Aug. 3, 1990, Pat. No. 5,095,104.

[51] Int. Cl.[5] ....................... A61K 31/70; C07H 13/02; C07H 15/04; C07H 23/00

[52] U.S. Cl. ....................................... 514/25; 536/4.1; 536/117; 536/118; 536/119; 536/120; 536/121; 536/122

[58] Field of Search ................ 536/4.1, 118, 122, 119, 536/117, 120, 121; 514/25

[56] References Cited

U.S. PATENT DOCUMENTS

| | | | |
|---|---|---|---|
| Re. 33,000 | 7/1989 | Gordon | 514/25 |
| 3,277,077 | 10/1966 | Holly et al. | 536/4.1 |
| 3,530,113 | 9/1970 | Rossi et al. | 536/4.1 |
| 3,586,664 | 6/1971 | Kohno et al. | 536/4.1 |
| 3,842,003 | 10/1974 | Netrli | 210/43 |
| 3,862,121 | 1/1975 | Jaques et al. | 260/210 R |
| 4,017,608 | 4/1977 | Gordon | 424/180 |
| 4,056,322 | 11/1977 | Gordon et al. | 536/4 |
| 4,192,868 | 3/1980 | Tronchet et al. | 536/4.1 |
| 4,251,520 | 2/1981 | Bruzzese et al. | 536/4.1 |
| 4,481,196 | 11/1984 | Teraji et al. | 536/4.1 |
| 4,735,934 | 4/1988 | Gordon | 514/25 |
| 4,738,953 | 4/1988 | Gordon | 514/25 |
| 4,835,264 | 5/1989 | Liav et al. . | |
| 4,968,790 | 11/1990 | DeVries et al. | 536/4.1 |
| 5,095,104 | 3/1992 | Gordon | 536/117 |

OTHER PUBLICATIONS

*Attorney's Dictionary of Patent Claims*, I. M. Aisenberg, vol. 1, Terminology, Matthew Bender (1992).

Cecil, *Textbook of Medicine*, 15th ed. Beeson et al., eds., W. B. Saunders Co., Philadelphia (1979) pp. 145-146.

*Fundamental Immunology*, 2nd ed., Paul ed., Rowen Press, New York (1986), pp. 721-733.

*Therapeutic Rheumatology*, Moll et al, eds., Raven Press, New York (1966) pp. 10-13.

*Primary Examiner*—Johnnie R. Brown

*Assistant Examiner*—Everett White

*Attorney, Agent, or Firm*—Welsh & Katz, Ltd.

[57] ABSTRACT

A glucofuranose derivative substituted at the 3,5,6- or 3,6-positions with a radical that provides an anionic charge at physiological pH values is disclosed, as are pharmaceutical compositions, and methods of making and using the same. The compounds are useful in treating inflammation, and particularly conditions that involve neutrophil influx; they are also useful in inhibiting gastric ulcer formation.

55 Claims, No Drawings

ANIONIC FURANOSE DERIVATIVES, METHODS OF MAKING AND USING THE SAME

CROSS-REFERENCE TO RELATED APPLICATION

This is a continuation-in-part application of co-pending application Ser. No. 07/563,103 filed on Aug. 3, 1990, now U.S. Pat. No. 5,095,104, whose disclosures are incorporated by reference.

TECHNICAL FIELD

The present invention relates to anionic furanose derivatives, and particularly to aldofuranose derivatives, containing a carbon atom skeleton having 5–7 carbon atoms, in which each of the 1- and 2-positions contains an electrically neutral substituent and in which two to four of the remaining skeletal carbon atoms bear an oxygen-linked radical that provides an anionic charge at physiological pH values, as well as to methods of making and using the same.

Background Art

Tissue injury can occur or be augmented when endogenous, cellular protective responses are 1) overwhelmed by endogenous or exogenous environmental factors, as loss of oxygen, or an extreme elevation of temperature, or when those protective responses are 2) suppressed, as by stress. Resulting tissue lesions can be a myocardial infarction, a burn, a stomach or duodenal ulcer, or, with the participation of immune and autoimmune response, can include lesions as diverse as allergic hives and rheumatoid arthritis. Also, the initial tissue injury, minor, trivial or otherwise, if begun by antihomeostatic factors, can be prolonged and complicated by the inflammation that it initiates.

The mammalian inflammatory response is a very complicated process, which, however always includes salient characteristics that can augment tissue injury. These include degrees of loss of microvessel integrity, in which there occurs 1) assaultative fenestration of the microvasculature, with accompanying leakage of the fluid elements of the blood into interstitial spaces, and 2) chemotactically directed migration of blood leukocytes into the inflamed tissues.

Inflammation can occur when the mammal's tissues are injured as by a bone break or sprain, ulceration or during reperfusion after an ischemic attack. In these instances, the inflammation is a response to one or more "self" molecules of the injured mammal. Inflammation can also occur by invasion of the mammalian tissues by "non-self" materials such as bacteria and dust particles in the lungs.

During an inflammatory response, chemical mediators such as histamine, 5-hydroxytryptamine, chemotactic factors, bradykinin, leukotrienes and prostaglandins are liberated locally. Phagocytic cells migrate to the area and cellular lysosomal membranes may be ruptured, releasing lytic enzymes.

On a macroscopic level, inflammation is accompanied by clinical signs such as erythema, swelling, pain and warmth.

Migration of leukocytes into an inflamed area is an important aspect of the inflammatory process. Of the leukocytes, T cells and phagocytic cells play a key role.

Of the phagocytic cells that migrate to a site of inflammation, neutrophils are among the most prominent in that those cells constitute about 45 to about 70 percent of all the leukocytes in an adult human. In addition, neutrophils not only phagocytose invading "non-self" substances, such as bacteria, but also secrete powerful redox agents, such as the superoxide anion radical, and secrete, as well, proteases and other lytic enzymes.

Phagocytic cells of the circulation are particularly drawn to sites of injury or bacterial infection by chemotactic factors that are generated from blood complement proteins or that are released by the injured cells or bacteria. Chemotaxis of phagocytic cells to the site of a bacterial infection is a desirable event in ridding the body of the invading microorganism.

However, chemotaxis and the resulting influx of phagocytic cells such as neutrophils to a site of injury can actually add to the injury due to the phagocytosis and secretions provided by the neutrophils. For example, Chan et al., *Neurobiology,* 34:315–320 (1984) reported on the damage caused to brain cells by the superoxide radical anion, hydrogen peroxide and hydroxyl radicals, and postulated that those oxygen-derived free radicals secreted by neutrophils play a role in cerebral ischemia and trauma. Similarly, the complement fragment C5a is a prime inducer of unwanted inflammation in diverse human disease conditions as in patients having had heart attacks that are treated with clot-lysing agents and enter the reperfusion period [Lucchesi, *Ann. Rev. Physiol.,* 52:561–576 (1990)] and in allergic states [Muller-Eberhard, Chapter 4, in *Textbook of Immunopathology,* Vol. 1, Miescher et al. eds., Grune & Stratton, New York (1968)]. C5a is a potent chemotactic agent for neutrophils.

It would therefore be beneficial if both loss of microvessel integrity and chemotaxis and neutrophil influx to a site of injury and incipient or established inflammation could be reduced or otherwise controlled.

BRIEF SUMMARY OF THE INVENTION

The present invention contemplates an aldofuranose ring compound whose carbon skeleton contains 5–7 carbon atoms. The 1- and 2-positions of such a compound have a substituent group, which is preferably oxygen-linked at both positions, that is electrically neutral at physiological pH values, with two through four of the remaining skeletal ring carbons as are present having an oxygen-linked radical that bears an anionic charge at physiological pH values, which charge is neutralized by a pharmaceutically acceptable cation.

It is preferred that a compound of the invention have a straight chain carbon skeleton.

One preferred group of the above anionic aldofuranose compounds is a compound of the chemical formula that corresponds to that of Formula A below.

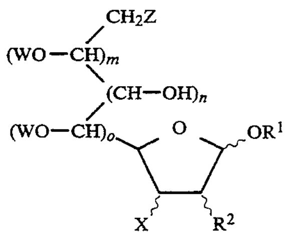

A wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5-9 carbon atoms in the ring;

OW is a radical having an anionic charge at physiological pH values;

X is H, OH or OW;

Z is H, OH or OW;

at least two OW groups are present;

m is zero or 1;

n is zero or 1; and o is zero, 1 or 2; such that a) the sum of m+n+o is zero, 1 or 2, and b) m is zero when n is zero.

Of the above preferred group of anionic aldofuranose compounds, a compound of the chemical formula that corresponds to that of Formula B below, is more preferred.

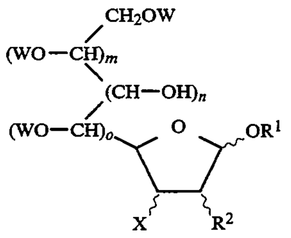

B wherein $R^1$ is selected from the group consisting of hydrogen, $C_1$-$C_6$ alkyl, $C_1$-$C_6$ acyl, benzyl and $C_1$-$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5-9 carbon atoms in the ring;

OW is a radical having an anionic charge at physiological pH values;

X is H, OH or OW;

at least two OW groups are present;

m is zero or 1;

n is zero or 1; and o is zero, 1 or 2; such that a) the sum of m+n+o is zero, 1 or 2, and b) when n is zero, m is zero.

Another preferred group of compounds has a chemical formula that corresponds to Formula C, below,

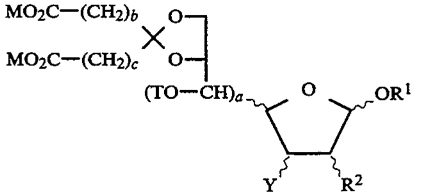

C wherein $R^1$ is selected from the group consisting of hydrogen, $C_1$-$C_6$ alkyl, $C_1$-$C_6$ acyl, benzyl and $C_1$-$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5-9 carbon atoms in the ring;

Y is H, OH, $OSO_3M$ or $OPO_3M$;

T is H, $SO_3M$ or $PO_3M$, and when T is other than H and Y is other than H or OH, OT and Y are the same;

a is zero or 1;

b is zero, 1, 2 or 3;

c is zero, 1, 2 or 3, with the sum of b+c being no more than 5; and

M is a physiologically acceptable cation.

Particularly preferred is a group of anionic aldofuranose derivatives that have a straight, 6-carbon chain, and have a structure that corresponds to Formula D, below,

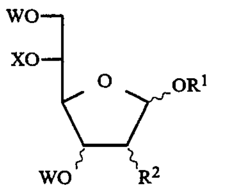

D wherein w is selected from the group consisting of $SO_3M$, $PO_3M_2$ and $R^6CO_2M$ in which $R^6$ is $(CH_2)_n$, where n is 1-5;

X is H or W;

$R^1$ is H or $C_1$-$C_6$ alkyl;

$R^2$ is H or $R^5$ wherein $R^5$ is OH or O-$C_1$-$C_6$ alkyl; or $R^1$ and $R^5$ together form a $CR^3R^4$ group in which (a) $R^3$ and $R^4$ are independently selected from H or $C_1$-$C_6$ alkyl with the total number of carbon atoms in $CR^3R^4$ being nine or fewer, or (b) $CR^3R^4$ together form an unsubstituted cycloaliphatic group containing a total of 5-9 carbon atoms in the ring; and M is a pharmaceutically acceptable cation.

Most preferably, a compound of the invention is an allo- or glucofuranose derivative, and that derivative is substituted at the 3,5,6- or the 3,6-positions with a radical that provides an anionic charge at physiological pH values. Such a compound has the structural Formula I

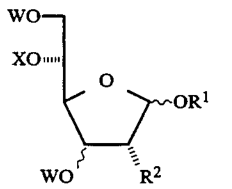

I wherein W is selected from the group consisting of $SO_3M$, $PO_3M_2$ and $R^6CO_2M$ in which $R^6$ is $(CH_2)_n$, where n is 1-5;

X is H or W;

each of the $R^1$ groups is independently H or $C_1$-$C_6$ alkyl, with the total number of carbon atoms in both $R^1$ groups being 9 or fewer; or the two $R^1$ groups together form a $CR^3R^4$ group in which (a) $R^3$ and $R^4$ are independently selected from H or $C_1$-$C_6$ alkyl with the total number of carbon atoms in $CR^3R^4$ being 9 or fewer, or (b) $CR^3R^4$ together from an unsubstituted cycloaliphatic group containing a total of 5-9 carbon atoms in the ring; and M is a pharmaceutically acceptable cation.

In a most preferred compound, W is a before-defined $SO_3M$ group where the substitution is at the 3,5,6-positions and $PO_3M_3$ wherein substitution is at the 3,6-positions. It is also preferred that the two $R^1$ groups together form a $CR^3R^4$ group in which $R^3$ and $R^4$ are the same alkyl group or hydrogen so that the $CR^3R^4$ group is symmetric. More preferred of those same $R^3$ and $R^4$ groups are hydrogen and $C_1$-$C_3$ alkyl, and most preferably, $R^3$ and $R^4$ groups are both $C_1$-$C_2$ alkyl groups. Thus, where the two $R^1$ groups together form a symmetric $CR^3R^4$ group (an alkylidene group), there are more preferably a total of 1 to 7 carbon atoms in the symmetric alkylidene group, and most preferably there are a total of 3 or 5 carbon atoms in the symmetric alkylidene group.

A pharmaceutical composition containing a before-defined compound as active agent is also contemplated. That pharmaceutical composition contains an anti-inflammatory or anti-ulcer effective amount of active agent dissolved or dispersed in a physiologically tolerable diluent. A pharmaceutical composition can be in solid or liquid form suitable for administration orally or parenterally.

A method of treating an inflammatory or gastric ulcer condition in a mammal is also contemplated. Here, an anti-inflammatory (anti-ulcer) or neutrophil-inhibiting amount of a before-described compound, typically present in a before-described pharmaceutical composition is administered to a mammal. Single and multiple administrations are contemplated.

The present invention has several benefits and advantages.

One benefit is that use of its method lessens swelling (edema) associated with inflammation.

Another benefit is that use of its method inhibits influx of neutrophils to a site of injury or other inflammation.

Yet another benefit of this invention is that its use inhibits gastric ulcer formation that can accompany use of indomethacin, and related NSAIDs.

An advantage of the invention is that the compounds are relatively non-toxic.

Another advantage of the invention is that the compounds are readily prepared from commercially available precursors.

Still further benefits and advantages will be apparent to a worker skilled in the art from the disclosure that follows.

DETAILED DESCRIPTION OF THE INVENTION

I. The Compounds

A. Anionic Sugars of the Art

A compound of the present invention is an aldofuranose derivative substituted with a radical that provides an anionic charge at physiological pH values. These compounds are discussed in detail hereinafter.

The principal pharmacologically active sulfated sugars of the art are polymers and include materials such as heparins, heparans and sulfates of dextran. Research results have indicated that the above polymers lose pharmacological activity as the polymer length decreases toward sulfated monomers. It was therefore unexpected that the compounds of the invention had pharmacological activity, and surprising that they are as potent as they are found to be. It is still further surprising that a compound of the invention lacks the anticoagulant activity that is so characteristic of the above polymers; that activity in the case of dextran sulfate having been shown to be an undesirable side effect when anti-viral activity was sought.

Another sulfated sugar of the art known generically as sucralfate is sucrose octakis-(hydrogen sulfate) aluminum complex sold under the trademark CARAFATE® by Marion Laboratories, Inc. This diglyceride contains a sulfate group in each of the eight sucrose hydroxyl groups.

The *Physicians' Desk Reference,* Medical Economics Co., Inc. Oradell, N.J. 1258–1259 (1990) indicates that sucralfate is only minimally absorbed from the gastrointestinal tract. This drug is said to form an ulcer-adherent complex with proteinaceous exudate at the ulcer site. In vitro and in vivo observations are said to suggest that sucralfate's anti-ulcer activity is the result of formation of an ulcer-adherent complex that covers the ulcer site and protects it from further attack by acid, pepsin, and bile salts.

A particularly useful group of new compounds of the invention are salts of 3,5,6-tri-O-sulfo-D-glucofuranose and its 1- and 2-ether derivatives. Different, known sulfated sugars, and particularly D-glucopyranose-1,3,6--trisulfate, as well as the trisulfates of D-mannose, D-galactose, and D-fructose are reported by Takiura et al., *Chem. Pharm. Bull.,* 18:429–435 (1970). A material referred to as glucose trisulfate also referred to as starch sulfate was also reported as useful in precipitating proteins from slaughterhouse wastes in a series of papers by Jorgensen [*Vatten,* 25(3):278–288 (1969); *Vatten,* 26(1):2–8 (1970); *Vatten,* 26(2):110–112 (1970); *Vatten,* 26(4):350–357 (1970); *Vatten,* 27(1):58–72 (1971); and *Vatten,* 29(1):4–051 (1971)]. Sulfated sucrose, lactose and starch are also reported as useful in waste precipitation in U.S. Pat. No. 3,842,003.

Mannose-6-phosphate is known to be useful in treating inflammation in experimental allergic encephalomyelitis (EAE), a cell-mediated autoimmune demyelinating disease of the central nervous system. Mannose-1,6-diphosphate and fructose-1,6-diphosphate, the only polyphosphate sugar esters studied, were reported to be less effective than mannose-6-phosphate in inhibiting the inflammation. [Willenborg et al., *FASEB J.,* 3:1968–1971 (1989).]

B. Compounds of the Invention

A compound of the invention is an anionic aldofuranose ring compound that contains a carbon atom skeleton having 5–7 carbon atoms. The carbon skeleton; i.e., the chain of carbon atoms that comprise the carbon atom portion of the ring plus any carbon atoms bonded directly thereto, is preferably a straight chain as are found in ribose, allose, glucose and rhamnose, but can also be a branched chain skeleton as is found in apiose.

A compound of the invention can therefore be looked at as a derivative of a pentose such as arabinose, lyxose, ribose and xylose or a hexose such as allose, altrose, galactose, glucose, gulose, idose, mannose, talose, or a heptose such as glycero-galacto-heptofuranose, qlycero-gluco-heptofuranose, glycero-ido-heptofuranose, glycero-allo-heptofuranose, glycero-talo-heptofuranose, glycero-manno-heptofuranose, glycero-gulo-heptofuranose, and glycero-altro-heptofuranose.

A compound of the invention can also be a derivative of a 2-deoxy pentose, a 2- or 3-deoxy or a 2,3-dideoxy hexose or heptose.

Although a compound of the invention can be viewed as a derivative of a natural sugar, a natural sugar can be a precursor for such a compound and is sometimes referred to herein as a precursor, a compound of the invention can be prepared by totally synthetic means from totally synthetic reagents. Natural sugars are thus utilized as common points of reference in discussing a compound of the invention.

An anionic aldofuranose compound of the invention has 1- and 2-position aldofuranose ring substituents that are electrically neutral at physiological pH values; i.e., the 1- and 2-substituents provide no electric charge at physiological pH values. The 1- and 2-positions are numbered following usual sugar ring numbering with the epimerizable carbon atom adjacent to the ring oxygen being the 1-position carbon atom.

The 2-position substituent can be a hydrogen (H), making the compound a 2-deoxyaldofuranose derivative. Preferably, however, the 2-position has an oxygen-linked electrically neutral substituent, and the discussion below will deal with the preferred 1- and 2-oxygen-linked substituents.

Thus, the 1- and preferably 2-position carbon atoms of a compound of the invention each have a substituent oxygen atom linked to a corresponding skeletal carbon atom with that substituent oxygen atom linked to another substituent that is electrically neutral at physiological pH values; i.e., pH 7.2–7.6. Exemplary electrically neutral substituents are discussed hereinafter.

A compound of the invention also contains two through four oxygen-linked substituent groups that exhibit an anionic charge at physiological pH values. The anionic charge or charges of the oxygen-linked radicals are neutralized by a proton or a pharmaceutically acceptable cation, as is discussed hereinafter. Having 5–7 carbon atoms in the skeleton, with two skeletal positions accounted for (positions 1 and 2) up to four other oxygen-linked positions are available for substitution, although only two such positions need be so substituted.

The anionic oxygen-linked substituents are present at the 3-, 5-, 6- and/or 7-positions as are present and available. A 3-deoxy derivative is also contemplated and although there is a 3-position carbon atom present, there is no oxygen available for substituent linkage in a 3-deoxy derivative. Similarly, a pentose derivative has no 6- or 7-position carbon atom that can be substituted, so those positions are neither present nor available for substitution with an anionic radical. Inasmuch as at least two anionic radicals (substituent groups) must be present, 3-deoxypentose derivatives are not contemplated.

Where a primary hydroxyl group is present in a precursor sugar molecule, that hydroxyl oxygen is usually substituted with an anionic group. A primary hydroxyl group can also be protected during synthesis by a well-known hydroxyl protecting group, e.g., an acetyl, benzyl or trimethylsilyl group, so that secondary or tertiary hydroxyl groups are reacted to form the at least two oxygen-linked anionic substituents, followed by removal of that protecting group to provide a compound of the invention that has a primary hydroxyl group.

A compound having a structure corresponding to chemical Formula A, below, is exemplary of that group of compounds that can include a primary hydroxyl group, a terminal methyl or an anionic radical-substituted primary hydroxyl group.

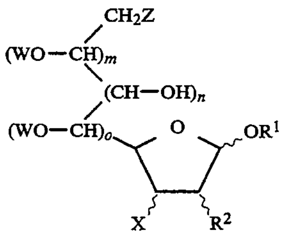

A wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

OW is a radical having an anionic charge at physiological pH values;

X is H, OH or OW;

Z is H, OH or OW;

at least two OW groups are present;

m is zero or 1;

n is zero or; and o is zero, 1 or 2; such that a) the sum of m+n+o is zero, 1 or 2, and b) m is zero when n is zero.

It is noted that the wavy line joining a group such as the 1-position $OR^1$ group to the ring in Formula A and the other formulas herein indicates that the stereochemistry can be either α or β. Where a bond is intended to be shown stereochemically, a bond that extends upwardly from the ring (β) is shown as a darkened wedge, whereas a bond extending downwardly from the ring (α) is shown as a dashed wedge. Following usual custom, ring-bonded hydrogen atoms are not illustrated for ease in understanding.

Inasmuch as an aldofuranose primary hydroxyl group is usually present and substituted with an anionic radical, a more preferred compound has a chemical formula that corresponds to that of Formula B, below.

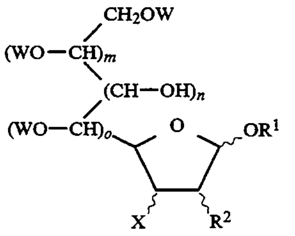

B wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

OW is a radical having an anionic charge at physiological pH values;

X is H, OH or OW;

at least two OW groups are present;

m is zero or 1;

n is zero or 1; and o is zero, 1 or 2; such that a) the sum of m+n+o is zero, 1 or 2, and b) when n is zero, m is zero.

A subgroup of the compounds discussed hereinabove are those in which the anionic radical is an ether-linked carbon-bonded carboxylate and the precursor primary hydroxyl and an adjacent secondary hydroxyl are substituted with such a group. A compound of this subgroup has a chemical formula that corresponds to Formula C, below.

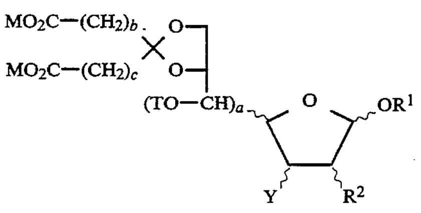

C wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

Y is H, OH, $OSO_3M$ or $OPO_3M$;

T is H, $SO_3M$ or $PO_3M$, and when T is other than H and Y is other than H or OH, OT and Y are the same;

a is zero or 1;

b is zero, 1, 2 or 3;

c is zero, 1, 2 or 3, with the sum of b+c being no more than 5; and

M is a physiologically acceptable cation.

It is thus seen that a compound of Formula C, above, has at least two skeletal oxygen substituents linked to the same, cyclic anionic radical, W, that itself contains two carbon-linked carboxylate groups.

A compound of the invention that contains six carbon atoms in the aldofuranose chain is particularly preferred. It is also particularly preferred that the aldofuranose skeleton be unbranched; i.e., a straight chain.

A group of particularly preferred compounds that exhibit both of the above preference have a chemical structure that corresponds to that shown in Formula D, below.

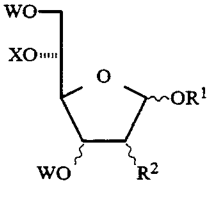

D wherein W is selected from the group consisting of $SO_3M$, $PO_3M_2$ and $R^6CO_2M$ in which $R^6$ is $(CH_2)_n$, where n is 1–5;

X is H or W;

$R^1$ is H or $C_1$–$C_6$ alkyl;

$R^2$ is H or $R^5$ wherein $R^5$ is OH or O-$C_1$–$C_6$ alkyl; or $R^1$ and $R^5$ together form a $CR^3R^4$ group in which (a) $R^3$ and $R^4$ are independently selected from H or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring; and M is a pharmaceutically acceptable cation.

A still more preferred group of compounds of the present invention are anionic allofuranose and glucofuranose derivatives. This more preferred group contains an allofuranose or glucofuranose substituted at the 3,5,6- or 3,6-positions by a radical that provides an anionic charge at physiological pH values, e.g., pH 7.2–7.4. The anionic proton or a pharmacologically acceptable counter ion (cation) M. These compounds have a structure that corresponds to that of Formula I, below, wherein $R^1$, W and X are as defined for Formula D.

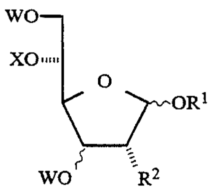

I

For other than 2-deoxy derivatives, the 1- and 2-positions of a before-described compound contain an oxygen-linked substituent group, and that group is electrically neutral; i.e., uncharged, at physiological pH values. Those 1- and 2-position oxygen-linked substituents can be the same or different although they are preferably the same.

In some embodiments, that oxygen-linked substituent group is hydrogen so that the 1- and 2-positions on the furanose ring contain hydroxyl groups. More preferably, the oxygen-linked substituent is an ether, and ester, a carbamate (carbamoyl or urethane) or most preferably, the 1- and 2-position substituents together with their oxygen atoms form an alkylidene bis-ether group. These substituents are discussed in detail below.

The non-hydrogen substituents of the $R^1$ and $R^5$ groups, being carbonaceous and uncharged at pH values of about 7.2–7.6, are relatively hydrophobic compared to hydrogen or a hydroxyl group of $R^1$ or $R^5$. That relative hydrophobicity is contrasted by the ionic charges of the substituents at the other substituted positions. Thus, an imaginary line can be drawn through the ring oxygen atom and the 2,3-carbon-carbon bond that divides the relatively hydrophobic and hydrophilic portions of a preferred aldofuranose of the invention.

Having one part of the aldofuranose hydrophobic and the other part hydrophilic provides polarity and a so-called hydrophobic moment to the molecule. Without wishing to be bound by theory, it is believed that the presence of such a hydrophobic moment assists in augmenting the activity of compounds having relatively hydrophobic $R^1$ and $R^5$ groups as compared to compounds where $R^1$ and $R^5$ are hydrogen or $R^5$ is hydroxyl.

When the 1- and 2-position hydroxyl groups are etherified, the non-furanose portion of the ether groups; i.e., $R^1$, is saturated or benzyl, and can contain a total of 9 or fewer, and preferably 1–7, carbon atoms. The non-furanose portion of an ether group is an alkyl, benzyl or alkylidene group.

An alkyl portion of the ether group can be exemplified by a $C_1$–$C_6$ alkyl group such as methyl, ethyl, isopropyl, sec-butyl, pentyl, hexyl, cyclopentyl or cyclohexyl. A benzyl ether group is also contemplated in addition to the $C_1$–$C_6$ alkyl ethers. For ease in synthesis, it is preferred that both 1- and 2-position groups be the same.

An alkylidene bis-ether is a ketal or an acetal. Symmetrical ketals prepared from unsubstituted cyclic ketones having 5–9 carbon atoms in the ring or ketones having an odd number of carbon atoms in a chain with the keto group at the central carbon (symmetric ketones) are preferred because of their relative ease of manufacture, since only one isomer is possible as compared with a ketal prepared from an unsymmetrical ketone or an acetal formed from an aldehyde other than formaldehyde. Exemplary alkylidene groups include methylene, 2-propylidene, 3-pentylidene, 4-heptylidene and 5-nonylidene, as well as cyclopentylidene, cyclohexylidene, cycloheptylidene, cyclooctylidene and cyclononylidene. An alkylidene group containing a total of 1 to 7 carbon atoms is preferred, whereas an alkylidene group containing 3–5 carbon atoms is more preferred.

A substituted furanose having a 1,2-ketal formed from acetone; i.e., a 2-propylidene (isopropylidene) group (3 carbon atoms), is particularly preferred.

Thus, when $R^1$ and $R^5$ of a prior chemical formula form an alkylidene group, that alkylidene group can be represented by the formula $CR^3R^4$. Here $R^3$ and $R^4$ are independently hydrogen or $C_1$–$C_6$ alkyl (as before) with the total number of carbon atoms in $CR^3R^4$ being nine or fewer. If the alkylidene group is formed from an unsubstituted cyclic ketone having 5–9 carbons in the ring, $R^3$ and $R^4$ together form an unsubstituted cycloaliphatic group containing a total of 5–9 carbon atoms in the ring. The structure of a $CR^3R^4$ group for a particularly preferred anionic allofuranose or glucofuranose derivative is shown below in Formula Ia,

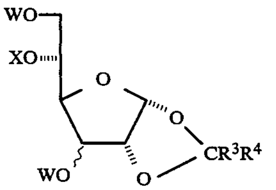
Ia wherein W is selected from the group consisting of $SO_3M$, $PO_3M_2$ and $R^6CO_2M$ in which $R^6$ is $(CH_2)_n$, where n is 1–5;

X is H or W;

$R^3$ and $R^4$ are independently selected from H or $C_1$–$C_6$ alkyl with the total number of carbon atoms in $CR^3R^4$ being 1–9, or (b) $CR^3R^4$ together form an unsubstituted cycloaliphatic group containing a total of 5–9 carbon atoms in the ring; and M is a pharmaceutically acceptable cation.

W is $SO_3M$ and X is W ($SO_3M$) in a most preferred compound of the above formula. In a particularly preferred compound, W is $PO_3M_1$ and X is H.

An $R^1$ or $R^5$ group substituent can also be a $C_1$–$C_6$ acyl group. A $C_1$–$C_6$ acyl group is an ester formed from the furanosyl hydroxyl group and a $C_1$–$C_6$ carboxylic acid. Exemplary $C_1$–$C_6$ ester groups include formate, acetate, propionate, butyrate, iso-butyrate, valerate, 3-methyl valerate, hexanate and cyclopentylcarboxylate.

A still further $R^1$ or $R^5$ group that is useful herein and is electrically neutral at physiological pH values is a $C_1$–$C_8$ carbamoyl group that has the structure C(O)N-$C_1$–$C_8$ alkyl or aryl, and forms a urethane link with the ring. These compounds are typically formed by reaction of a $C_1$–$C_8$ alkyl or aryl isocyanate with the hydroxyl groups at the 1- and/or 2-positions. The contemplated $C_1$–$C_8$ alkyl groups are those discussed before further including heptyl, octyl and the like groups. Aryl carbamates containing up to 8 carbon atoms are also contemplated. Exemplary compounds can be prepared using phenylisocyanate, m-tolylisocyanate, p-tolylisocyanate and 2,4-dimethylphenylisocyanate for reaction with a hydroxyl group. The carbamoyl carbonyl carbon is not included in counting the carbon atoms of a $C_1$–$C_8$ carbamoyl group.

A compound of the invention bears an anionic charge at physiological pH values. That anionic charge is measured as the potassium salt of the furanose derivative.

The radical that provides anionic charge at physiological pH values as the potassium salt (the anionic radical) can be at any two or more of the 3-, 4-, 5-, 6- and/or 7-positions as are present and available. As noted earlier, where a compound of the invention is a pentose derivative, an anionic radical must be present at the 3-position as well as at the 5-position to provide the required at least two anionic radicals. A hexose or heptose derivative can be a 3-deoxy compound having the at least two anionic radicals at the 5- and 6-positions (hexose), the 5- and 7-positions (heptose), 6- and 7-positions (heptose) or 5-, 6- and 7-positions (heptose).

The anionic radical depicted as OW in the formulas is a sulfate ester (sulfate, or sulfo radical) or a phosphate ester (phosphate or phosphono radical), or an ether-linked carbon-bonded carboxylate whose anionic charge is neutralized by a pharmaceutically acceptable non-toxic cation. Sulfo (sulfate) radicals are particularly preferred.

When a carboxyl radical (carboxylate group) is present, that radical is bonded to a carbon atom and separated from the ether-linking aldofuranose oxygen atom by at least one carbon atom, and preferably by one to five methylene ($CH_2$) groups. In one embodiment, the carbon-bonded carboxylate is a part of simple ether group bonded to a furanose ring-substituted oxygen atom as in the structure $-O-CH_2CO_2^-$. In another embodiment, the carboxylate is part of a bis-ether dicarboxylate as was shown before in Formula C.

The preparation of the variously substituted anionic furanose compounds is discussed in greater detail hereinafter.

The anionically charged radical as utilized, can be neutralized by a pharmaceutically acceptable non-toxic cation, and as such, a compound as used need not itself be anionic at physiological pH values. Exemplary pharmaceutically acceptable non-toxic cations include the proton, metal ions such as sodium, potassium, calcium magnesium, $zinc^{II}$, $iron^{II}$, $iron^{III}$ and $aluminum^{III}$, as well as amine salts such as the glucosammonium and mono-, di- or tri-ethanolammonium ions and the ammonium ion ($NH_4^+$) itself. Sodium and potassium salts of an anionic aldofuranose derivative are most preferred as is a complex of aluminum as can be formed using anhydrous aluminum chloride.

An aluminum complex of a trisulfate compound such as Compound III typically contains about 25 to about 55 weight percent aluminum, and about 6 to about 11 percent sulfur per molecule. Proportional amounts of aluminum and sulfur, when present, are present in an aluminum complex of one of the other compounds of Formula A.

A pharmaceutically acceptable non-toxic cation is often referred to in the chemical formulas herein as M. In those formulas, M is given a valence of +1 for convenience although it is to be understood that M can also be multivalent as is the case with calcium, magnesium, zinc, iron and aluminum. The hydrates of those cations often shown as hydroxides such as hydrated aluminum ions like $Al(OH)^{+2}$ are also contemplated to be within the ambit of a pharmaceutically acceptable non-toxic cation and the designation M.

An aluminum complex useful here is readily prepared. In an exemplary preparation for a trisulfate aldofuranose, a solution of a soluble aluminum salt such as anhydrous aluminum chloride is admixed with the aldofuranose trisulfate. The pH value of the admixture is adjusted to about 3 to about 5, and the admixture is stirred for a time sufficient to form a desired complex, which typically precipitates from the admixture. The precipitate is then collected.

The soluble aluminum salt and trisulfate can be admixed in a mole ratio of about 5:1 to about 1:2. It is also helpful to admix methanol with the precipitate and to wash the precipitate with methanol as that solvent dissolves the aluminum hydroxide that can form during the reaction. Aluminum complexes of the other compounds of Formula A are similarly prepared.

Each compound useful herein is a furanose. Both the D- and L-series of furanose compounds are contemplated, although the D- series is particularly preferred.

Exemplary compounds of the invention, including most preferred and particularly preferred compounds of the D- series, and whose structures correspond to Formula I, are illustrated below, in which M is as discussed before, and are identified by Roman numerals. A compound of the prior art, Compound VII, is also shown for purposes of illustration only. The names for those compounds are listed beneath the structures, adjacent to corresponding Roman numerals, using the potassium salts as exemplary.

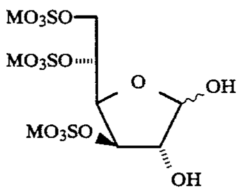
II

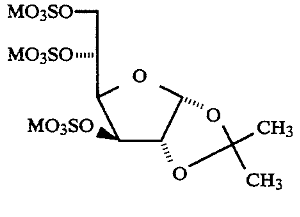
III

-continued

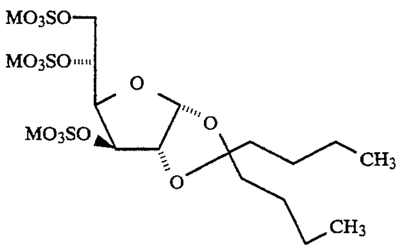
IV

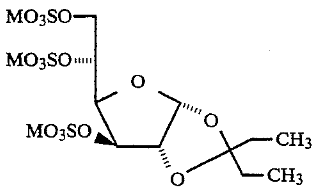
V

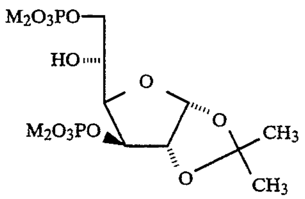
VI

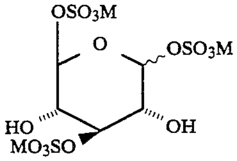
VII

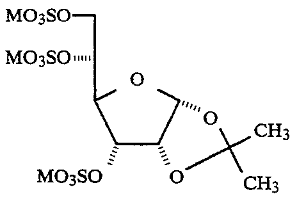
VIII

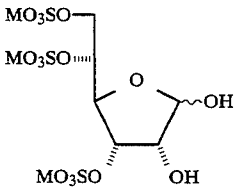
IX

II. 3,5,6-Tri-O-sulfo-α-D-glucofuranose, tripotassium salt.

III. 1,2-O-(2-Propylidene)-3,5,6-tri-O-sulfo-α-D-glucofuranose, tripotassium salt.

IV. 1,2-O-(5-Nonylidene)-3,5,6-tri-O-sulfo-α-glucofuranose, tripotassium salt.

V. 1,2-O-(3-Pentylidene)-3,5,6-tri-O-sulfo-α-D-glucofuranose, tripotassium salt.

VI. 1,2-O-(2-Propylidene)-3,6-di-O-phospho-α-D-glucofuranose, tetrapotassium salt.

VII. 1,3,6-Tri-O-sulfo-α-D-glucopyranose, tripotassium salt, a compound of the prior art utilized for purposes of comparison. This compound was prepared by the procedure of Takiura et al., *Chem. Pharm. Bull.*, 18:429–435 (1970).

VIII. 1,2-O-(2-Propylidene)-3,5,6-tri-O-sulfo-α-D-allofuranose, tripotassium salt.

IX. 3,5,6-Tri-O-sulfo-α-D-allofuranose, tripotassium salt.

Further specific compounds of the invention are illustrated in the table below for the compounds of Formula A, where M is as before defined.

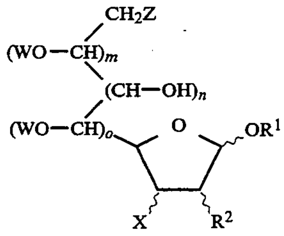

A

| Compounds of Formula A | | | | | | |
|---|---|---|---|---|---|---|
| $R^1$* | $R^2$* | Z | m(W)** | n | o(W)** | X |
| H | H | $OSO_3M$ | 0 | 0 | 2($SO_3M$) | $OSO_3M$ |
| $CR^3R^4(CH_2)$ | | OH | 0 | 1 | 1($SO_3M$) | $OSO_3M$ |
| $CR^3R^4[C(CH_3)_2]$ | | $OSO_3M$ | 1($SO_3M$) | 1 | 0 | $OSO_3M$ |
| $CR^3R^4[C(CH_3)_2]$ | | $OSO_3M$ | 1($SO_3M$) | 1 | 0 | H |
| $CH_3$ | $OCH_3$ | $OSO_3M$ | 0 | 0 | 2($SO_3M$) | $OSO_3M$ |
| $R^3R^4[C(C_4H_9)_2]$ | | H | 0 | 0 | 2($SO_3M$) | $OSO_3M$ |
| $C_5H_{11}$ | H | H | 0 | 0 | 2($SO_3M$) | $SO_3M$ |
| $C(O)CH_3$ | $OC(O)CH_3$ | $OSO_3M$ | 1($SO_3M$) | 1 | 0 | $OSO_3M$ |
| Bz | H | $OSO_3M$ | 1(OH) | 1 | 0 | $OSO_3M$ |
| $C(O)NCH_3$ | $OC(O)NCH_3$ | $OSO_3M$ | 0 | 0 | 1($SO_3M$) | $OSO_3M$ |
| $R^3R^4[C(CH_3)_2]$ | | H | 0 | 0 | 1($SO_3M$) | $SO_3M$ |
| $CH_3$ | $OCH_3$ | $CH_2CO_2H$ | 0 | 0 | 1($CH_2CO_2M$) | $CH_2CO_2M$ |
| $C_4H_9$ | $O_4CH_9$ | $OSO_3M$ | 0 | 0 | 1($SO_3M$) | $OSO_3M$ |
| H | H | $OSO_3M$ | 0 | 0 | 1($SO_3M$) | $OSO_3M$ |
| $C(O)C_4H_9$ | $OC(O)C_4H_9$ | $OSO_3M$ | 0 | 0 | 1($SO_3M$) | $OSO_3M$ |
| Bz | OBz | $OPO_3M$ | 0 | 1 | 0 | $OPO_3M$ |
| $C(O)NC_4H_9$ | $OC(O)NC_4H_9$ | $OSO_3M$ | 0 | 0 | 1($SO_3M$) | $OSO_3M$ |
| $CR^3R^4[C(C_2H_5)]$ | | $OSO_3M$ | 0 | 0 | 1($SO_3M$) | H |
| $C_3H_7$ | $OC_3H_7$ | $OPO_3M_2$ | 0 | 1 | 0 | $OPO_3M_2$ |
| $C_2H_5$ | H | $OPO_3M_2$ | 0 | 1 | 0 | $OPO_3M_2$ |
| $C_6H_{13}$ | H | $OSO_3M$ | 0 | 0 | 0 | $OSO_3M$ |
| $CR^3R^4[C(CH_3)]$ | | $OPO_3M_2$ | 0 | 0 | 0 | $OPO_3M_2$ |
| $CR^3R^4$[(Cyclo $C_6$)] | | $(CH_2)_4CO_2M$ | 0 | 0 | 0 | $(CH_2)_4CO_2M$ |
| $C(O)C_6H_{13}$ | $OC(O)C_6H_{13}$ | $OSO_3M$ | 0 | 0 | 0 | $OSO_3M$ |
| Bz | H | $OPO_3M$ | 0 | 0 | 0 | $OPO_3M$ |
| $C(O)NC_6H_{13}$ | $OC(O)NC_6H_{13}$ | $OSO_3M$ | 0 | 0 | 0 | $OSO_3M$ |

*Where $R^1$ and $R^5$ together form a $CR^3R^4$ group, the presence of that group is noted by an indented "$CR^3R^4$", followed by the identity of the $CR^3H^4$ group in parenthesis or brackets. "Cyclo $C_6$" indicates that $CR^3R^4$ forms a ketal made from a cyclohexanone. "Bz" indicates a benzyl group. A parenthesized "O" is a carbonyl oxygen atom.
*Where $R^1$ and $R^5$ together form a $CR^3R^4$ group is noted by an indented "$CR^3R^4$", followed by the identity of the $CR^3H^4$ group in parenthesis or brackets. "Cyclo $C_6$"
**The identity of the radical "W" is noted in parenthesis when m or o is other than zero (0).

Still further compounds of the invention are illustrated in the table below for the compounds of Formula C, which, while being in a subclass of those compounds of Formula A, are more readily illustrated using Formula C, and where M is as previously defined.

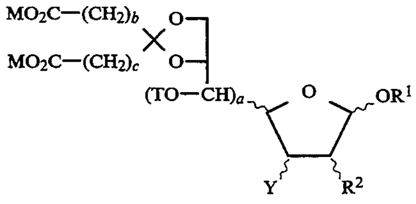

C

| Compounds of Formula C | | | | | |
|---|---|---|---|---|---|
| $R^1$* | $R^2$* | Y | a(T)** | b | c |
| H | H | H | 1(H) | 1 | 1 |
| $R^3R^4[C(CH_3)_2]$ | | OH | 1(H) | 2 | 1 |
| $C(O)CH_3$ | $OC(O)CH_3$ | $OSO_3M$ | 1($SO_3M$) | 2 | 2 |

-continued

| Compounds of Formula C | | | | | |
|---|---|---|---|---|---|
| $R^1$* | $R^2$* | Y | a(T)** | b | c |
| Bz | OBz | OH | 1(H) | 3 | 1 |
| $C(O)NCH_3$ | $OC(O)NCH_3$ | $OSO_3M$ | 0 | 2 | 2 |
| $C(O)NC_6H_{13}$ | $OC(O)NC_6H_{13}$ | $OSO_3M$ | 0 | 1 | 1 |
| $C(O)C_5H_{11}$ | $OC(O)C_5H_{11}$ | $OSO_3M$ | 0 | 0 | 1 |
| H | H | H | 0 | 1 | 1 |
| $CH_3$ | H | $OSO_3$ | 0 | 1 | 1 |
| $R^3R^4$[(Cyclo $C_5$)] | | OH | 0 | 1 | 1 |

*Where $R^1$ and $R^5$ together form a $CR^3R^4$ group, the presence of that group is noted by an idented "$CR^3R^4$", followed by the identity of the $CR^3R^4$ group in parenthesis or brackets. "Cyclo $C_5$" indicates the $CR^3R^4$ form a ketal made from cyclopentanone. "Bz" indicates a benzyl group. A parenthesized "O" is a carbonyl oxygen atom.
**The identity of the radical "W" is noted in parenthesis when m or o is other than zero (0).

II. Compositions and Methods

A before-described compound has pharmaceutical properties in treating inflammatory or ulcerative and related conditions, as is discussed hereinafter. When used in treatment such as to treat inflammation or ulcer, an anti-inflammatory amount of a compound is dissolved or dispersed in a physiologically tolerable (pharmaceutically acceptable) diluent to form a pharmaceutical composition.

A compound of the invention is effective when administered orally and also when administered parenterally. Oral administration is the preferred mode of administration.

Liquid compositions and tablets or other dosage forms are preferably themselves buffered to provide a physiological pH value when administered or upon dissolution. For preparations designed to dissolve in the stomach, provision of physiological pH values of less import since the stomach and gastrointestinal tract provide their own pK values and buffering systems.

When the compound is to be administered orally, it can be admixed with a filler and/or binder such as starch and a disintegrator, and the admixture can be pressed into a tablet of a size convenient for administration orally. The solid, particulate compound can also be placed into a capsule. Alternatively, a water solution or suspension of an acid, salt or complex, or an admixture thereof with a flavored syrup such as cherry syrup, can be administered orally.

When a compound is administered parenterally as by injection or intravenously, it is usually dissolved in a physiological saline solution that contains sodium chloride in sufficient concentration to make the overall solution to be injected isotonic to body fluids. In treating some patients or when convenient, a compound in aqueous solution can also be administered by nasopharyngeal spray. Administration also can be by means of a suppository in patients unable to retain medication administered by mouth. Suitable pharmaceutically acceptable carriers and techniques in addition to those mentioned above, as are well known, can be used when desired.

The dosage can be varied over extremely wide limits, as a compound is effective at low dosage levels and is relatively nontoxic and free of adverse side effects. A compound can be administered in the minimum quantity which is effective; i.e., in an amount sufficient to reduce or inhibit inflammation, gastric ulcer formation, neutrophil influx to a site of inflammation or to treat a gastric ulcer that is present, collectively referred to as an anti-inflammatory effective amount, unless a specific treatment is discussed. The dosage can be increased as desired up to the maximum effective dosage tolerated by the patient.

A compound is usually administered in an amount of about 0.1 to about 150 milligrams (mg), or preferably at about 1 to about 50 mg, per kilogram (kg) of body weight per day, and more preferably in an amount of about 10 to about 50 mg/kg of body weight per day, over the period required for treatment.

A compound of the invention is utilized in a method of treating an inflammatory condition, however, produced; i.e., by external injury, autoimmunity or the like, ulcerative or neutrophil influx condition in a mammal such as a laboratory animal, like a mouse, rat or rabbit, a veterinary animal like a dog, horse or cow, or a primate such as a human or ape. In accordance with this method, a compound of the invention is administered to a mammal in need thereof in an anti-inflammatory amount. The compound is maintained within the treated mammal until the compound is excreted or metabolized by usual bodily means.

The compound is administered in a previously discussed pharmaceutical composition. A single dose administration can be utilized, but in general practice, multiple doses over a several day time period are used, with the treatment continuing until the treated condition such as inflammation ceases.

A method of the present invention is useful in treating inflammation generally, as well as specifically where neutrophils are or may be implicated. For example, a compound of the invention can be used to lessen the edema associated with an inflammatory condition. Edema can be caused by a complement component such as fraction C5a as induced by zymosan or other agent, as well as by non-complement-related inflammatory agents such as trypsin, collagenase and carrageenan. A compound of the invention is shown hereinafter to be useful in reducing the edema caused by C5a (zymosan), trypsin, bacterial collagenase and carrageenan.

In addition, a compound of the invention acts to inhibit neutrophil chemotaxis, thereby inhibiting influx of neutrophils to a site of injury or other inflammation. For example, clot-lysing enzymes such as t-PA, urokinase and streptokinase as are utilized in treatment of heart attacks can lead to ischemic inflammation once the blood starts flowing after a clot is lysed. Compounds of the invention are shown hereinafter to be useful in reducing swelling during post-ischemic reperfusion.

The drug allopurinol is often utilized to suppress experimental reperfusion injury. That drug is utilized near its toxic level at about 20–30 mg/kg. A compound of the present invention can achieve a similar result to that achieved by allopurinol, but at a much lower dose; i.e., 0.1–0.2 mg/kg, injected intraperitoneally. The dose of one compound used to achieve that result in rats was about 1/1000 the $LD_{50}$ value for mice.

In vitro studies show that compounds of this invention are more active in inhibiting neutrophil chemotaxis than the anion channel blockers probenecid and SITS (4-acetamido-4'-isothiocyano-stilbene-2,2'-disulfonate), and are more effective than are ibuprofen and prednisone. Prostaglandin $E_2$ ($PGE_2$) was about equally as active as Compound III, and Compound III was more active than any of the other assayed compounds. These results parallel assays for neutrophils present in vivo in inflamed tissues.

A compound of this invention can also be used to treat gastric ulceration. Here, gastric ulcers were induced in laboratory rats by a combination of stress caused by injection of zymosan and zymosan-activated serum into rat paws, and the administration of indomethacin. Ulcer reduction using the same stimulus and either 17.5 mg/kg of Compound III or 25 mg/kg cimetidine was greater using Compound III than cimetidine.

A compound of the present invention was also shown to be useful in inhibiting gastric ulceration in rats when induced by a) ethanol, b) ethanol plus heparin, c) stress plus ethanol plus heparin, and d) indomethacin, following inflammatory stress induced by the serial paw injections of zymosan and zymosan-activated serum (ZAS). Here, ethanol alone produced ulcers in rat stomachs, and the number of ulcers produced was reduced by administration of a compound of the invention. Administration of ethanol plus heparin induces production of ulcers 24 hours after administration, many of which bleed. Treatment with a compound of the invention again reduced the number of ulcers produced, and no bleeding ulcers were observed.

Non-steroidal anti-inflammatory drugs (NSAIDs) such as aspirin, indomethacin and ibuprofen have proven to be extremely useful analgesics that on prolonged use often induce gastric pathology such as bleeding and erosion of the stomach lining. It is surprisingly found that administration of both an NSAID in its regularly useful amount and a compound of this invention in an anti-inflammatory amount can inhibit or lessen that NSAID-induced gastric pathology.

III. Compound Synthesis

A compound of the present invention can be readily prepared from commercially available precursors. Several useful precursors are available from Pfanstiehl Laboratories, Inc., Aldrich Chemical Co. and Sigma Chemical Co.

Synthesis of the precursor sugars is readily accomplished by known means. Each of the 5-carbon natural sugars is available from the Aldrich Chemical Co., as are the 1,2-O-isopropylidene derivatives of D-glucofuranose, L-idofuranose and D-xylofuranose. Five of the eight $C_6$-sugars are also available from Aldrich, as they are also available from Sigma Chemical Co., which also offers D- and L-isomers of the remaining three $C_6$-sugars, altrose, idose and talose. Pfanstiehl Laboratories, Inc. also offers 1,2:5,6-di-O-isopropylidene-α-D-allofuranose, di-O-isopropylidene-α-D-apiose, 1,2:3,4-di-O-isopropylidene-α-D-glucofuranose as well as the 1,2-O-mono-isopropylidene derivative. 1,2-O-Isopropylidene-β-L-idofuranose and the similarly substituted derivative of D-xylofuranose are available from Sigma Chemical Co., as is methyl deoxyribofuranoside.

Each of the above compounds can be selectively blocked and deblocked with hydroxyl group protecting agents so that a desired compound can be synthesized.

The 7-carbon sugar precursors can be prepared from the corresponding appropriately protected 5-carbon sugars following the procedures of Brimacomb et al., *Carbohydr. Res.*, 150:35–51 (1986). In accordance with those procedures a pentose-1,5-dialdehyde is prepared from the aldopentofuranoside by periodate oxidation. The resulting 1,5-dialdehyde is then reacted with formylmethylenetriphenylphosphorane in boiling benzene to form a corresponding enal. The enal derivatives are then catalytically osmylated as discussed below, to provide the corresponding heptose derivative that can be further reacted or protected as desired.

Catalytic osmylation is carried out as follows. A solution of the olefinic sugar (1 equivalent), N-methylmorpholine N-oxide (2 equivalents), and osmium tetroxide (0.05–1 equivalents) in acetone-water (8:1, 5 ml/mmole of olefinic sugar) is stirred at room temperature until the reaction is complete, as by thin layer chromatography or other assay method. The reaction typically takes 3–6 hours. The reaction mixture is then diluted with a solvent such as chloroform (50 ml/mmole of starting olefinic sugar), washed with 5M hydrochloric acid (2 ml/mmole of starting olefinic sugar), and shaken vigorously for several minutes with aqueous 45 percent sodium metabisulfite (3 ml/mmole of starting olefinic sugar). The organic solution is dried and concentrated under reduced pressure and passed down a silica gel column with ethyl acetate to remove inorganic impurities. The product(s) of the reaction is (are) then recovered by usual means such as high pressure liquid chromatography, crystallization, column or thin layer chromatography.

More specific syntheses of the particularly preferred and most preferred allofuranose and glucofuranose compounds of the invention are discussed hereinafter as illustrative.

The glucofuranose 3,5,6-tri-sulfate derivatives are particularly preferred compounds of the invention. A typical synthesis is discussed below using 1,2-O-(isopropylidene)-3,5,6-D-glucofuranose trisulfate, Compound III, as exemplary.

1,2-O-Isopropylidene-α-D-glucofuranose (Compound A) is commercially available from Pfanstiehl, and can also be prepared from commercially available 1,2,5,6-diisopropylidene-D-glucose (diacetone-D-glucose) by mild acid hydrolysis. Compound A is dissolved in anhydrous pyridine with vigorous stirring, and the resulting solution is cooled to about −30° C. in a dry ice/acetone bath.

Excess chlorosulfonic acid in an inert solvent such as chloroform, tetrahydrofuran (THF) or methylene chloride is admixed portion-wise with the pyridine solution, while maintaining the temperature of the resulting reaction mixture between about −30° and −15° C. The reaction mixture is permitted to warm to room temperature after all of the chlorosulfonic acid has been added and the resulting exotherm has subsided.

Aliquots are thereafter taken and assayed for completeness of reaction using electrophoresis. After the reaction is complete, the reaction mixture is again cooled in a dry ice/acetone bath to a temperature below about −15° C., and a mixture of water and pyridine (about 1:4, v/v) is added to decompose the excess chlorosulfonic acid.

In one procedure, barium hydroxide is added to a pH value up to about 7.0 to precipitate the sulfate ion generated by the excess chlorosulfonic acid. After removal of the precipitate, solid carbon dioxide (dry ice) is added to remove most of the barium ions present. The resulting precipitate is filtered and the filtrate is concentrated to dryness.

The dried filtrate is dissolved in water and passed through an ion exchange resin, potassium form, to form the tripotassium salt. Replacement of potassium ion by sodium or ammonium ions in the resin and passage of the redissolved filtrate over the column provides the corresponding sodium or ammonium salts. The resulting aqueous eluate is then concentrated in vacuo and purification of the desired compound can be achieved by recrystallization as with methanol/water.

More preferably, the pyridine/water solution obtained after decomposition of the excess chlorosulfonic acid is concentrated in vacuo to provide a viscous oil that is usually brown in color. Addition of an aqueous solution of an appropriate cation hydroxide such as potassium hydroxide to a pH value of about 6.5–7 provides the desired cation without the need for using barium. Concentration of the cation hydroxide solution followed by recrystallization as above provides the desired compound as white crystals.

The allofuranose derivative VIII is similarly prepared.

The corresponding disulfate can be prepared by stopping the above sulfonation prior to completion of the sulfonation reaction and separating out the disulfate as by preparative electrophoresis. The disulfate is more preferably prepared by use of only two moles of chlorosulfonic acid per mole of Compound A.

Compounds having hydroxyl groups at the 1- and 2-positions ($R^1$ is H and $R^2$ is $OR^5$, where $R^5$ is H in Formulas A–D and I, and in Compound II), as well as those compounds having different groups bonded to the oxygens of the 1- and 2-positions are typically prepared from the anionic group-substituted furanose such as the above-prepared trisulfate. For example, Compounds II and IX, before, are prepared by acid hydrolysis of Compounds III and VIII, respectively, followed by neutralization with an appropriate cation hydroxide such as potassium hydroxide.

The hydroxyl groups of the 1- and 2-positions of an anionic furanose such as Compounds II and IX can thereafter be reacted as desired to provide the other than hydrogen $R^1$ and $R^5$ groups of a compound of Formulas A–D or I. It is often more convenient, particularly where $R^1$ and $R^5$ together form an alkylidene group, to link the $R^1$ and $R^5$ substituents prior to adding the anionic radicals.

For example, where $R^1$ and $R^5$ together form a 3-pentylidene group, a sugar such as D-glucose is reacted with excess 3-pentanone in the presence of zinc chloride and an acid to form the 1,2:5,6-di-O-(3-pentylidene)-α-D-glucofuranose derivative. That compound can then be partially deblocked with mild acid to form the 1,2-O-(3-pentylidene) derivative that is reacted with a source of the anionic radical, e.g., chlorosulfonic acid, neutralized with an appropriate cation hydroxide and then crystallized as discussed before.

1,2-$C_5$–$C_9$ Cyclic alkylidene derivatives are also preferably prepared by formation of the 1,2:5,6-di-O-cyclic alkylidene-aldofuranose in a manner analogous to that discussed immediately above.

In another procedure that is particularly useful for preparation of the 1,2-O-(5-nonylidene)glucofuranose derivatives, D-glucurono-6,3-lactone is utilized as the starting material. The 1,2-O-(5-nonylidene) group is added as discussed before for other ketones. The resulting 1,2-O-(5-nonylidene)-D-glucurono-6,3-lactone is then reduced with borane in THF or another solvent to provide the corresponding glucofuranose derivative that is thereafter reacted with an appropriate source of the anionic radical to form the desired compound.

A compound of the invention wherein $R^1$ and $R^5$ are $C_1$–$C_6$ alkyl is typically prepared by first preparing an appropriate 1- and 2-substituted pyranose, which is thereafter converted to a corresponding furanose such as glucofuranose, and then to a 3,5,6-trisubstituted or 3,6-disubstituted derivative, as desired. An exemplary synthesis for a 1,2-dialkoxy-glucofuranose is discussed below.

3,4,6-Tri-O-benzyl-D-glucal is prepared from commercially available 3,4,6-tri-O-acetyl-D-glucal (Aldrich Chemical Co.) using the method of Blackburne et al., *Aust. J, Chem.,* 29:381 (1976). The 3,4,6-tri-O-benzyl-D-glucal is coupled with an alcohol whose alkyl portion is the $R^1$ $C_1$–$C_6$ alkyl group using the method described in Friesen et al., *J. Am. Chem. Soc.,* 111:6656 (1989), which coupling forms a corresponding 1-α-$C_1$–$C_6$ alkoxy-2-β-iodo-glycoside. Briefly, the glycal and an excess of the alcohol are stirred in methylene chloride in the presence of molecular sieves to which solid I(sym-collidine)$_2$-$ClO_4$ is added to effect haloetherification. [See also, Lemieux et al., *Can. J. Chem.,* 43:2190 (1965), and the citations therein.]

The β-iodo group in the above glycoside is replaced with inversion of configuration by reaction with a metal salt of an alcohol whose alkyl portion is the $R^2$ $C_1$–$C_6$ alkyl group. Thus, a 2-O-$C_1$–$C_6$-alkyl-3,4,6-tri-O-benzyl-1-$C_1$–$C_6$-glucoside is formed.

The benzyl groups are thereafter removed by standard procedures, as by hydrogenolysis, to form a 2-O-$C_1$–$C_6$alkyl-1-$C_1$–$C_6$-glucoside, which is in the glucopyranoside form. The formed glucopyranoside can be converted into the glucofuranoside by using the method described in Yamaguchi et al., *Carbohydrate Research,* 59:129 (1977).

Briefly, a glucopyranoside is stirred in an alcohol solvent in the presence of an acid catalyst such as Amberlite® CG-120(H+). The alcohol solvent used contains the same $C_1$–$C_6$ alkyl group as is present in the $R^1$ alkyl group. The resulting furanoside is recovered and α- and β-anomers are typically separated. The resulting furanoside is thereafter reacted with an appropriate reagent to form a desired anionic glucofuranose, as is also discussed herein.

Compounds having a phosphate monoester as the anionic group are typically prepared from the corresponding compound whose 1- and 2-position hydroxyl groups are etherified, or whose 2-position is deoxy. Here, for example, diphenyl chlorophosphate is the source of the anionic radical. The resulting phosphate triester is hydrogenated over platinum to cleave the phenyl ester groups from phosphorus atom. Neutralization of the phosphoric acid ester with an appropriate cation hydroxide provides the desired compound.

Where a compound having the structure of Formula C is desired, a similar reaction scheme can be followed for reaction of the 1- and 2-positions above up to the addition of the anionic radical. Here, the 1,2-di-reacted, e.g. 1,2-O-(3-pentylidene) or 1,2-O-(2-propylidene), or the like, derivative is reacted with ketodicarboxylic acid containing a total of three to six carbon atoms; i.e., b+c of Formula D is no more than five. Exemplary keto diacids include oxomalonic acid, oxalacetic acid, 3-ketoglutaric acid, 2-ketoglutaric acid, 2-oxoadipic acid and 3-oxoadipic acid. The ketal is formed as is any ketal by usual procedures.

A compound containing a carboxyl anionic group is exemplified by the carboxymethyl derivative. Here, a compound such as Compound A is reacted with hydroxide ion in the presence of a halo-substituted carboxylic acid such as an omega-halo carboxylic acid like chloroacetic acid to effect etherification of the sugar hydroxyl groups. The cation of the hydroxide ion utilized in the reaction is typically the ultimately desired cation so that cation exchange is unnecessary. The produced carboxylate is then recovered by chromatography and/or crystallization.

A compound having an $C_1$–$C_6$ acyl group as $R^1$ and an O-$C_1$–$C_6$ acyl group as $R^2$ ($OR^5$), as well as a compound having a $C_1$–$C_8$ carbamoyl and/or O-$C_1$–$C_8$ carbamoyl group, is most readily prepared by adding the anionic radicals to an aldofuranoside whose 1- and 2-positions are protected from reaction, deprotecting the 1- and 2-positions and then adding the acyl or carbamoyl groups back to the 1- and 2-position oxygen atom(s), as available. Any hydroxyl group desired to be present at any of the 3-, 5-, 6- and/or 7-positions should be suitably protected during the acylation (carbamoylation) reaction and deprotected thereafter.

Suitable acylating reagents are well known and include the acid halides and anhydrides such as acetyl chloride and propionic anhydride. Carbamoylation is most conveniently carried out using the corresponding isocyanate derivative. Reaction conditions for acylation and carbamoylation are well known and need not be gone into herein.

Best Mode for Carrying Out the Invention

Materials and Methods

Nuclear magnetic resonance (NMR) spectra were recorded by means of a Varian XL-300 spectrometer. Optical rotations were measured on a Perkin Elmer Model 241 polarimeter using a 1 dm microcell. Decomposition points were determined in capillary tubes on a Mel-Temp II melting point apparatus from Laboratory Devices (Holliston, Me.).

Thin layer chromatographs (TLC) were developed on 5 cm glass slides coated with 0.25 mm silica gel 60 $F_{254}$ supplied by E. Merck. The solvent system used in TLC studies was n-propanol/ethyl acetate/water/ammonium hydroxide (5:2:2:1). Compounds were visualized by charting with a 10 percent aqueous solution of sulfuric acid.

Paper electrophoresis studies were performed using an EC135 power supply and an EC370 minicell from E-C Apparatus Corporation (St. Petersburg, Fl.). In each study, a potential of 200 V was applied for 30 minutes on Whatman chromatography paper (3 mm Chr; cat. #3030861) cut to 6 cm×14 cm. The buffer used was acetic acid-pyridine (pH 6.5), prepared by mixing 0.05M acetic acid with pyridine. Compounds were detected by spraying the paper with 2 percent aniline hydrogen phthalate reagent and heating to 150° C. for 20 minutes. Migration values (M) were determined relative to a glucose-6-sulfate standard.

Atomic absorption (AA) experiments were performed by Schwarzkopf Microanalytical Laboratory (Woodside, N.Y.). Elemental analyses were carried out by Midwest Microlab (Indianapolis, Ind.).

Example 1: 1,2-O-(2-Propylidene)-3,5,6-tri-O-Sulfo-D-Glucofuranose, Tripotassium Salt (Compound III)

1,2-O-Isopropylidene-α-D-glucofuranose [100 grams (g); 0.45 moles] was dissolved in anhydrous pyridine [1 liter (1)] with vigorous stirring, and the resulting solution cooled to about −30° C. in a dry ice/acetone bath. Chlorosulfonic acid [185 g; 1.59 moles, d=1.753 g/ml] in chloroform (570 ml) was added in portions while maintaining the resulting reaction mixture at a temperature of about −30° to about −15° C. The temperature of the reaction mixture was permitted to rise to room temperature over a period of about 15–20 hours.

The progress of sulfonation is monitored by paper electrophoresis and thin layer chromatography (TLC). The TLC solvent used was 5:3:1:1 (v/v) n-propanol:ethyl acetate:water:ammonium hydroxide. Recovery of the reaction product began after all of the disulfate product had been converted to trisulfate.

With the temperature of the reaction mixture again cooled to below about −15° C., water (55 ml) in pyridine (200 ml) was added slowly to the reaction mixture to decompose the excess chlorosulfonic acid. Two recovery processes were used.

Recovery #1

This recovery method is a modification of that described by Whistler et al., *Methods in Carbohydrate Chemistry,* Vol. 2, Academic Press, New York (1963) for the preparation of D-glucose-6-sulfate.

The above reaction mixture was warmed to room temperature and adjusted to pH 7 by the addition of saturated barium hydroxide. About 10 l of $Ba(OH)_2$ solution was required. A white precipitate of $BaSO_4$ was formed. Care was taken to maintain the pH value at about 7 as higher pH values lead to product degradation and a brown coloration.

The resulting solution was concentrated in vacuo to about 2 l at 35° C. The solid was removed by filtration. Solid $CO_2$ (dry ice) was added to the filtrate to precipitate $BaCO_3$, which was filtered off, and the filtrate was concentrated in vacuo to dryness.

A Dowex 50X8-200 ion exchange resin, hydrogen form, was prepared. The dried filtrate, above, was dissolved in a minimum amount of water and applied to the column. The acidic eluant was collected and neutralized to a pH value of 7, and then concentrated in vacuo at 35° C.

The resulting product was recrystallized three times from methanol/water. Yield=47 g (18 percent), as a white crystalline solid.

Analytical analysis:

TLC $R_f$=0.3; M (glucose-6-sulfate)=1.6; decomposition point 190° C.; Ba analysis by AA<42 ppm; $[\alpha]_D^{25}$-5.3° (C 0.8, $H_2O$); $^1H$ NMR ($D_2O$, chemical shifts relative to TMSPA δ 6.10 (d, 1H), 5.09 (d, 1H), 4.90 (d, 1H), 4.89–4.83 (m, 1H), 4.70–4.66 (m, 1H), 4.57–4.52 (m, 1H), 4.26–4.21 (m, 1H), 1.55 (s, 3H), 1.39 (s, 3H). Analysis calculated for $C_9H_{13}K_3O_{15}S_3$: C, 18.81; H, 2.28; S, 16.74. Found: C, 17.52; H, 2.29; S, 15.39.

Recovery #2

Another sample of the sulfonation reaction product was prepared, treated with water/pyridine as before and warmed to room temperature. The reaction mixture was concentrated in vacuo at 35° C. to form a brown, viscous oil. That oil was then neutralized directly with a 1 molar (M) aqueous KOH solution to a pH value of 6.5–7. That solution was reconcentrated in vacuo at 35° C. to provide an off-while solid. That solid was recrystallized as above to provide high purity, white crystals. Yield=132 g (51 percent).

Analytical analysis:

TLC $R_f$=0.3; M (glucose-6-sulfate)=1.6; decomposition point 190° C.; $[\alpha]_D^{25}$-5.5° (C 2.0, $H_2O$); $^1H$ NMR ($D_2O$, chemical shifts relative to TMSPA δ 6.10 (d, 1H), 5.09 (d, 1H), 4.90 (d. 1H), 4.89–4.83 (m, 1H), 4.70–4.66 (m, 1H), 4.57–4.52 (m, 1H), 4.26–4.21 (m, 1H), 1.55 (s, 3H), 1.39 (s, 3H). Analysis calculated for $C_9H_{13}K_3O_{15}S_3$: C, 18.81; H, 2.28; S, 16.74. Found: C, 18.43; H, 2.21; S, 15.69.

Example 2: 3,5,6-Tri-O-Sulfo-α-D-Glucofuranose, Tripotassium Salt (Compound II)

A solution of 1,2-O-(2-isopropylidene)-3,5,6-tri-O-sulfo-α-D-glucofuranose, tripotassium salt (15 g, 26 mmole) (Compound III) in 0.2M sulfuric acid (500 mL) was stirred and heated at 40° C. for 10 hours. Analysis of the reaction mixture by TLC and paper electrophoresis indicated that hydrolysis was complete.

The reaction mixture was allowed to cool to ambient temperature and was then neutralized to pH 7 by the portionwise addition of a saturated barium hydroxide solution. The formed precipitate was removed by filtration and the solution was concentrated under reduced pressure to one-half of its original volume. Additional precipitate was removed by filtration. Carbon dioxide was then added to the filtrate and the newly formed precipitate was also removed by filtration. The resulting filtrate was concentrated under reduced pressure to leave a yellow, viscous oil.

The product was applied to an ion exchange column which was prepared using Dowex 50X8-200 ($H^+$ form) ion exchange resin. Following elution with water, the fractions containing the desired product were combined and neutralized to pH 7 by adding 1M potassium hydroxide solution. The solvent was then removed under reduced pressure.

The product was dissolved in the minimum quantity of water and methanol was added gradually. The purified potassium salt of the trisulfate was precipitated as an amorphous powder. This procedure was repeated two additional times to yield 8.9 g (64 percent) of a slightly hygroscopic light beige powder: TLC $R_f$=0.2; M (glucose-6-sulfate)=1.6; decomposition point 190° C.; $^1H$ NMR ($D_2O$, chemical shifts relative to TMSPA) δ 5.55 (d, 1H), 5.36 (d, 1H), 4.98–4.54 (m, 2H), 4.50–4.08 (m, 3H). Analysis calculated for $C_6H_9K_3O_{15}S_3$: C, 13.48; H, 1.70; S, 17.99. Found: C, 14.14; H, 2.16; S, 14.62.

Example 3: 1,2:5,6-Di-O-(3-pentylidene)-α-D-glucofuranose

To anhydrous dextrose (26.5 g, 147 mmole) in freshly distilled 3-pentanone (285 g, 3.31 moles) was added zinc chloride (31.8 g, 233 mmole) which had been freshly fused and pulverized. With vigorous stirring, phosphoric acid (99 percent) (0.53 g, 5.4 mmole) was added.

Stirring was continued and the mixture was heated to 40° C. for 48 hours.

After cooling to ambient temperature, the solids were removed by filtration and rinsed with ethylene dichloride. Solid sodium carbonate was added to the filtrate until a pH of 7.5 was reached. This mixture was again subjected to filtration. The collected solids were diluted with an equal volume of ethylene dichloride and a 20 percent aqueous solution of sodium bicarbonate was added. The solids which were formed were removed by filtration and the organic layer was separated and extracted two additional times with 10 percent sodium bicarbonate solution. The organic extract was washed once with water, dried over anhydrous magnesium sulfate, filtered, and concentrated under reduced pressure to leave a viscous yellow oil.

The crude product was distilled under high vacuum and the desired compound distilled at 150°-160° C. (0.20 mm Hg) as a light yellow viscous oil. From the distillation, 9 g (20 percent) of the product was obtained: TLC $R_f$(hexane/ethyl acetate, 3:1)=0.25.

Example 4: 1,2-O-(3-Pentylidene)-α-D-glucofuranose

To a mixture of methanol (75 ml) and 0.8 percent aqueous sulfuric acid (75 ml) was added 1,2:5,6-di-O-(3-pentylidene)-α-D-glucofuranose (14 g, 44 mmole). The solution was stirred at ambient temperature for 20 hours.

The reaction mixture was then neutralized to pH 7 with barium carbonate. The mixture was filtered and the filtrate was concentrated under reduced pressure to leave an off-white solid.

The product was recrystallized twice from ethyl acetate/methanol to afford 6.8 g (63 percent) of a white crystalline solid: TLC $R_f$ (hexane/ethyl acetate, 3:1)=0.08.

Example 5: 1,2-O-(3-Pentylidene)-3,5,6-tri-O-sulfo-α-D-glucofuranose, tripotassium salt (Compound V)

A solution of 1,2-O-(3-pentylidene)-α-D-glucofuranose (6.8 g, 28 mmole) in dry pyridine (60 ml) was vigorously stirred and cooled to −30° C. A solution of chlorosulfonic acid (16 g, 138 mmole) in chloroform (35 ml) was added dropwise, while keeping the temperature of the reaction mixture between −30° C. and −15° C. After the addition was complete, the reaction mixture was allowed to gradually warm to ambient temperature over a 15-18 hour time period.

When analysis by TLC and paper electrophoresis indicated that sulfation was complete, the reaction mixture was cooled to −15° C. and treated according to the procedure outlined in Example 1.

After completing the ion exchange chromatography, the fractions containing the desired product were combined and neutralized to pH 7 by adding 1M potassium hydroxide solution. The solvent was then removed under reduced pressure.

The product was recrystallized twice from a methanol/water mixture to yield 8.7 g (46 percent) of a white crystalline solid: TLC $R_f$=0.5; M (glucose-6-sulfate)=1.6; decomposition point 180° C.; $^1$H NMR ($D_2O$, chemical shifts relative to TMSPA) δ 6.10 (d, 1H), 5.05 (d, 1H), 4.88 (d, 1H), 4.82-4.69 (m, 2H), 4.55-4.45 (m, 1H), 4.24-4.12 (m, 1H), 1.78 (q, 2H), 1.63 (q, 2H), 0.91 (t, 3H), 0.83 (t, 3H).

Example 6: 1,2-O-(5-Nonylidene)-α-D-glucofuranurono-6,3-lactone

A mixture of 2-mesitylenesulfonic acid (3.5 g, 14.8 mmole), 1,4-dioxane (360 ml), and triethyl orthoformate (46.8 g, 316 mmole) was cooled to zero degrees C. Freshly distilled 5-nonanone (351 g, 2.47 mole) was added dropwise. The reaction mixture was allowed to warm to ambient temperature and then stirred for an additional two hours.

Powdered D-glucofuranurono-6,3-lactone (35.0 g, 200 mmole) was added and the mixture was vigorously stirred until a clear solution was obtained (approximately 24 hours). The reaction mixture was then heated at 45° C. for 48 hours.

The resulting mixture was neutralized with triethylamine to a pH value of 7, filtered to remove unreacted starting material, and concentrated under reduced pressure. The resulting yellow-orange oil was diluted with chloroform and filtered to remove undissolved solids. The filtrate was washed with water, dried over anhydrous magnesium sulfate, filtered, and concentrated under reduced pressure.

The concentrated material crystallized on standing. The solid was broken up in hexane and collected by filtration to yield 18.5 g (31 percent) of a white crystalline solid: TLC $R_f$ (methylene chloride/methanol, 9:1, with a drop of acetic acid) 0.5; $^1$H NMR ($CDCl_3$, chemical shifts relative to TMS) δ 6.03 (d, 1H), 5.02-4.89 (m, 1H), 4.87-4.72 (m, 2H), 4.65-4.42 (br s, 2H), 3.48-3.25 (br s, 1H), 1.80-1.64 (m, 2H), 1.61-1.50 (m, 2H), 1.45-1.33 (m, 8H), 1.08-0.81 (m, 6H).

Example 7: 1,2-O-(5-Nonylidene)-α-D-glucofuranose

A solution of 1,2-O-(5-nonylidene)-α-D-glucofuranurono-6,3-lactone (17.37 g, 58 mmole) in anhydrous THF (350 ml) was cooled to −70° C. with a dry ice/acetone bath. A 1.0M solution of borane in THF (300 ml, 300 mmole) was then added dropwise while maintaining the temperature of the reaction mixture below −40° C.

The reaction mixture was allowed to stir for 48 hours at ambient temperature, then cooled to zero degrees C., and methanol (300 ml) was added dropwise. Upon warming to room temperature, the mixture was stirred for 2 hours and then concentrated under reduced pressure.

The product was recrystallized from THF/hexane to yield 12 g (69 percent) of a white solid: TLC $R_f$(hexane/ethyl acetate, 1:1)=0.2; $^1$H NMR ($D_6$-DMSO, chemical shifts relative to TMS) δ 5.84 (d, 1H), 5.00 (d, 1H), 4.61 (d, 1H), 4.41 (d, 1H), 4.22-4.18 (m, 2H), 4.01-3.96 (m, 1H), 3.92-3.79 (m, 1H), 3.76-3.76 (m, 1H), 3.56-3.47 (m, 1H), 1.68-1.57 (m, 6H).

Example 8: 1,2-O-(5-Nonylidene)-3,5,6-tri-O-sulfo-α-D-glucofuranose, tripotassium salt (Compound IV)

A solution of 1,2-O-(5-nonylidene)-α-D-glucofuranose (7.0 g, 23 mmole) in dry pyridine (90 ml) was vigorously stirred and cooled to −30° C. A solution of chlorosulfonic acid (9.8 g, 84 mmole) in chloroform (30 ml) was added dropwise while keeping the temperature of the reaction mixture between −30° C. and −15° C. After the addition was complete, the reaction mixture was allowed to gradually warm to ambient temperature over a 15-18 hour time period.

When analysis by TLC and paper electrophoresis indicated that sulfation was complete, the reaction mixture was cooled to −15° C., and treated according to the procedure outlined in Example 1, Recovery 1.

After completing the ion exchange chromatography, the fractions containing the desired product were combined and neutralized to pH 7 by adding 1M potassium hydroxide solution. The solvent was then removed under reduced pressure.

The product was recrystallized twice from a methanol/water moisture to yield 11.5 g (75 percent) of a white crystalline solid: TLC $R_f$=0.5; M (glucose-6-sulfate)=1.4; decomposition point of 180° C.; $^1H$ NMR ($D_2O$, chemical shifts relative to TMSPA) δ 6.08 (d, 1H), 5.06 (d, 1H), 4.86 (d, 1H), 4.83–4.67 (m, 2H), 4.53–4.48 (m, 1H), 4.22–4.16 (m, 1H), 1.81–1.73 (m, 2H), 1.66–1.58 (m, 2H), 1.39–1.22 (m, 8H), 0.91–0.83 (m, 6H).

Example 9: 1,2-O-(Isopropylidene)-3,6-di-O-(diphenylphospho)-α-D-glucofuranose

A solution of 1,2-O-(isopropylidene)-α-D-glucofuranose (6.2 g, 28.2 mmole) in anhydrous pyridine (90 ml) was cooled to zero degrees C. in an ice bath under a nitrogen atmosphere. Diphenyl chlorophosphate (25 g, 93.1 mmole) was added dropwise with vigorous stirring. After warming to ambient temperature, the reaction mixture was heated at 50° C. for 72 hours.

Upon completion of the reaction, $H_2O$ (3 ml) was slowly added to the mixture. The reaction mixture was then filtered and concentrated under reduced pressure to leave a viscous brown oil.

The oil was taken up in ethyl acetate and this solution was washed sequentially with a 0.5M hydrochloric acid solution, a saturated sodium bicarbonate solution, and water. The organic layer was dried over anhydrous sodium sulfate, filtered, and concentrated under reduced pressure.

The product was purified by column chromatography using silica gel 60 and a solvent system of methylene chloride: methanol (9:1, viv). The fractions containing the desired product were combined and concentrated under reduced pressure to yield 5.6 g (38 percent) of an off-white solid: TLC $R_f$ (methylene chloride:methanol, 9:1)=0.3; $^1H$ NMR ($CDCl_3$, chemical shifts relative to TMS) δ 7.38–6.85 (m, 2OH), 5.58 (d, 1), 5.28 (br s, 1H), 4.89–4.75 (m, 1H), 4.53–4.33 (m, 2H), 4.03–3.92 (m, 1H), 3.70–3.57 (m, 1H), 2.98 (br s, 1H), 1.36 (s, 3H), 1.19 (s, 3H).

Example 10: 1,2-O-(2-Propylidene)-3,6-di-O-phospho-α-D-glucofuranose, tetrapotassium salt (Compound VI)

To a solution of 1,2-O-(isopropylidene)-3,6-di-O-(diphenylphospho)-α-D-glucofuranose (1.4 g, 2.6 mmole) in ethanol (25 ml) were added 90 mg of platinum oxide. The suspension was shaken under 50 psi of hydrogen gas for 24 hours. The solution was then filtered through celite and the celite was rinsed with additional ethanol.

The filtrate was concentrated under reduced pressure, the residue was dissolved in water, and the solution was neutralized to pH 8 by adding a 1M potassium hydroxide solution. This solution was concentrated under reduced pressure to yield 0.8 g (83 percent) of a white solid: TLC $R_f$=0.2; M ) glucose-6-sulfate)=1.3; decomposition point 140° C.; $^1H$ NMR ($D_2O$, chemical shifts relative to TMSPA) δ 6.08 (d, 1H), 4.92–4.55 (m, 3H), 4.42–4.38 (m, 1H), 4.29–4.16 (m, 1H), 3.85–3.77 (m, 1H), 1.52 (s, 3H), 1.35 (s, 3H).

In the following examples, proton magnetic resonance (Pmr) spectra were recorded by means of a Nicolet 200 MHz spectrometer. Chemical shifts are reported in ppm downfield from internal tetramethysilane (TMS).

Reaction mixtures and products were routinely analyzed by high performance liquid chromatograph (HPLC) using a Bio-Rad Isocratic Model 1306 instrument with an ultraviolet (UV) detector set at a wavelength of 210 nm. The column used was a commercially available Lichrosorb Si-60 (5μ) normal phase silica gel column. The mobile phase was composed of acetonitrile, water, and ammonium hydroxide in the ratio by volume of 45:5:1, respectively.

Thin layer chromatographs (TLC) were developed on 10 cm glass slides coated with silica gel and a fluorescent indicator. Spots were visualized by charring after immersion in a 10 percent aqueous solution of sulfuric acid. The solvents used in developing TLC plates were: Solvent A—ethyl acetate; Solvent B—hexane/ethyl acetate (3:1).

Specific rotations were determined at 20° C. with a Rudolph Research Autopol II Polarimeter or at 23° C. with a Perkin-Elmer Model 241 Polarimeter.

Example 11: 1,2:5,6-Di-O-Cyclohexylidene-α-D-glucofuranose

To 758 g (7.7 moles) of cyclohexanone were added 260 g (1.44 moles) of anhydrous dextrose, followed by 20 ml of concentrated sulfuric acid. The mixture was heated to 35° C. and monitored by TLC. The flow rate of the desired product using Solvent A was $R_f$=0.95.

When the reaction was complete, the solution was cooled to 20° C. and carefully neutralized with excess potassium hydrogen carbonate to a pH of 9. The mixture was filtered and an equal volume of water was added. This mixture was concentrated under reduced pressure until a precipitate had begun to form. An equal volume of water was added and the mixture was extracted twice with ethylene dichloride. The combined organic extracts were washed twice with saturated aqueous sodium sulfate, filtered, and concentrated under reduced pressure to leave a heavy syrup. The syrup was diluted with hexane and allowed to cool slowly to 4° C. The crystalline product was filtered by suction filtration, washed with cold hexane, and dried under a vacuum at 40° C.

The melting point of the compound 1,2:5,6-di-O-cyclohexylidene-α-D-glucofuranose was 132°–124° C. The optical rotation of the compound was $[\alpha]^{20}_D$ (C2, EtOH)=−2.4°.

Example 12: 1,2:5,6-Di-O-cyclopentylidene-α-D-glucofuranose

To 70 g (0.389 mol) of anhydrous dextrose in 800 g (9.51 moles) of freshly distilled cyclopentanone were added 84 g (0.616 mol) of zinc chloride that had been freshly fused and pulverized. This mixture was stirred vigorously and 1.4 g (0.014 mol) of phosphoric acid (99 percent) were added. Stirring was continued and the mixture was heated to 40° C. for 48 hours.

After cooling to 25° C., the solids were removed by suction filtration and rinsed with ethylene dichloride. Solid sodium carbonate was added to the filtrate until a pH value greater than 7 was reached. This mixture was again subjected to suction filtration. The filtrate was diluted with an equal volume of ethylene dichloride and a 10 percent aqueous solution of sodium bicarbonate was added. The solids formed were removed by suction filtration and the organic layer was separated and extracted two additional times with 10 percent sodium bicarbonate solution. The organic extract was washed once with water, dried over anhydrous magnesium sulfate, filtered, and concentrated under reduced pressure to leave a viscous brown oil.

Upon distillation of the brown oil, 1,2:5,6-di-O-cyclopentylidene-α-D-glucofuranose distilled at 150°–170° C. as a light yellow viscous oil. With TLC analysis, the flow rate of this compound using Solvent B was $R_f$=0.21.

Example 13: 1,2:5,6-Di-O-butylidene-α-D-glucofuranose

To 36 g (200 mmol) of anhydrous dextrose were added 144 g (2.0 moles) of butyraldehyde. The mixture was stirred at 0° C. and 10 ml (120 mmol) of concentrated hydrochloric acid was added dropwise over a 15 minute period. The temperature of the reaction mixture rose to 43° C. and then dropped to 35° C. where it was maintained by means of a heating mantle for 3 hours.

After stirring about 15-18 hours at 25° C., the reaction mixture was neutralized with saturated sodium bicarbonate solution and extracted twice with toluene. The combined organic extracts were dried over anhydrous magnesium sulfate, filtered, and concentrated under reduced pressure to leave a light yellow viscous oil.

This residue was purified by high vacuum distillation and 1,2:5,6-di-O-butylidene-α-D-glucofuranose was obtained as the fraction boiling at 170°-210° C. (0.15 mm Hg). Analysis of the distillate indicated that the desired product was obtained as a mixture of isomers in a total purity greater than 97 percent. Pmr ($CDCl_3$) δ 6.00-5.82 (m, 1H), 5.45-4.84 (m, 4H), 4.72-2.95 (m, 5H), 1.83-1.22 (m, 8), 1.18-0.78 (m, 6H).

Example 14: 1,2:5,6-Di-O-(4-heptylidene)-α-D-glucofuranose

To 510 g (4.47 moles) of 4-heptanone were added 40 g (255 mmol) of anhydrous dextrose. The mixture was stirred and 55 g (403 mmol) of freshly fused and pulverized zinc chloride and 0.92 g (9.3 mmol) of phosphoric acid (99 percent) were added. Stirring was continued and the mixture was heated to 40° C. for 48 hours.

After cooling to 25° C., the reaction mixture was treated as discussed in Example 12.

With TLC analysis, the flow rate of 1,2:5,6-di-O-(4-heptylidene)-α-D-glucofuranose using Solvent B was $R_f$=0.28.

A compound of the invention is prepared by suitable reaction of a compound prepared in Examples 11-15 as discussed elsewhere herein.

Example 15: Aluminum Complex of 1,2-O-(1-Isopropylidene)-3,5,6-Tri-O-Sulfo-D-Glucofuranose (Compound III:Al)

A. Synthesis

Five preparations of Compound III:Al are discussed below that produce complexes having slightly different percentages of ingredients, but that are substantially equivalent in pharmacological activity in ulcer paradigms:

Preparation 1: A solution of anhydrous $AlCl_3$ (3.0 g) in 129 ml of water was brought to a pH value of 4.26 with 51.0 ml of 1N NaOH. Compound III (2.25 g) dissolved in 129 ml of water was added to the $AlCl_3$ solution and the resulting admixture was mixed for one hour at room temperature. The resulting precipitate was harvested 20 hours later, and yielded 1.89 g.

Preparation 2: The above amounts of anhydrous $AlCl_3$ and Compound III each in 129 ml of water were admixed, and the resulting admixture was adjusted to a pH value of 4.26 with 45 ml of 1N NaOH. The pH-adjusted admixture was stirred for one hour and then methanol (61 ml; 20 percent of the original volume) was added. The precipitate was harvested 20 hours later, and yielded 1.26 g.

Preparation 3: Four preparations similar to Preparation 1 were made with 20 volume percent methanol being added after one hour of mixing. The precipitates from those four reactions were harvested about 20 hours later by filtration through a #5 filter paper. The combined precipitates were washed first with 20 percent (v/v) ethanol in water and then 100 percent methanol to yield 7.5 g of the complex after drying.

Preparation 4: The above amounts of anhydrous $AlCl_3$ in 129 ml $H_2O$ was brought to a pH value of 4.26 with 47.3 ml of 1N NaOH. The sodium salt of Compound III (2.048 g) dissolved in 129 ml of water was added to the $AlCl_3$ solution and the resulting admixture was mixed for one hour. Methanol (61 ml; 20 percent of the original volume) was then added. The precipitate was harvested 20 hours later, and yielded 1.83 g.

Preparation 5: A solution of anhydrous $AlCl_3$ (1.0 g) in 129 ml $H_2O$ was brought to a pH value of 4.26 with 51.0 ml of 1N NaOH. Compound III (4.50 g) dissolved in 129 ml of $H_2O$ was added to the $AlCl_3$ solution and the resulting admixture was mixed for one hour. The resulting precipitate was harvested 20 hours later.

When the pH value of an above $AlCl_3$ solution (e.g. Preparation 1) is raised to 4.26 in the absence of Compound III and methanol addition, a precipitate is produced weighing about 1.4 g. That precipitate is presumed to be $Al(OH)_3$ since that material is water-insoluble whereas the aluminum hydroxychlorides are soluble in water.

Admixture of 20 volume percent methanol to a suspension of the $Al(OH)_3$ precipitate results in almost complete dissolution of the precipitate, leaving only about 50 mg of precipitate undissolved. Since that undissolved amount of precipitate is less than about 0.5 percent of the yield of complex obtained using a methanol washing step, it is believed that the precipitate observed in the presence of Compound III is a substantially single entity coordination complex, and not a mixture of precipitates.

This view is supported by the titration data reported below.

Below are the elemental analyses, in per cent:

| Preparation # | C | H | Al | Na | K | Cl |
|---|---|---|---|---|---|---|
| 1 | 6.95 | 3.96 | 20.1 | 1.5 | 0.4 | 7.50 |
| | 6.72 | 3.89 | — | — | — | 7.69 |
| 2 | 8.10 | 3.93 | 20.35 | — | 3.72 | 7.87 |
| | 7.89 | 4.10 | 20.50 | — | 3.73 | 7.90 |
| 3 | 7.01 | 4.15 | 22.3 | 0.4 | 0.00 | 2.66 |
| | 7.20 | 4.23 | — | — | — | 3.06 |
| 4 | 8.08 | 4.12 | 17.8 | 1.3 | — | 6.63 |
| | 7.87 | 4.12 | — | — | — | 6.71 |
| 5 | 11.96 | 4.15 | 14.7 | 0.2 | 0.4 | 1.44 |
| | 11.88 | 4.09 | — | — | — | 1.64 |

With the introduction of end-stage washes, it was noted that sodium and potassium can be virtually washed out of the precipitate but that chloride cannot. The residual chloride is assumed to be a component of the coordination compound that forms. In calculating the moles of chloride per mole Compound III in the complex, chloride equivalents equal to the residual sodium+potassium still found were subtracted, under the assumption that this much chloride is a counterion for these contaminating cations.

| Relative Composition in Moles | | | | | |
|---|---|---|---|---|---|
| | Preparation # | | | | |
| | 1 | 2 | 3 | 4 | 5 |
| Compound III | 1 | 1 | 1 | 1 | 1 |
| Aluminum | 11.8 | 10.2 | 12.6 | 8.9 | 5.0 |
| Chloride | 2.4 | 1.7 | 1.1 | 4.5 | 1.0 |

-continued

| | | | | | |
|---|---|---|---|---|---|
| Hydroxide | 30.0 | 25.9 | 33.7 | 19.2 | 13.0 |

Note: The relative content of hydroxide equivalents is calculated by difference, as that number required to balance the aluminum positive charges, in association with the three monoionic sulfates of Compound III and chloride.

| Compound III as Percent of Coordination Compound<br>Preparation # | |
|---|---|
| 1 | 29% |
| 2 | 34% |
| 3 | 30% |
| 4 | 34% |
| 5 | 50% |

The relative composition data reported above suggest that one of the determinants of compound composition is the nature of the Compound III alkali metal counterion, sodium apparently reducing the amount of aluminum that is interactive with Compound III in the complex, and the content of hydroxide. This composition difference may relate to the tendency of sodium ion and not potassium ion to interact with oxygens via an ion-dipole bond, as exemplified by its hydration, and by its capacity to reduce the activity coefficient of molecular oxygen.

The resulting modulation of hydroxide content is not without significance for an anti-ulcer drug. These results would indicate that the potassium salt of Compound III is the preferred starting material.

B. Determination of the Aluminum Coordination in Sucralfate and Compound:Al III by Solid-State High Resolution $^{27}$Al NMR An NMR technique has been in use that permits identification of the number of coordination partners possessed by aluminum cations in aluminum-oxygen compounds. (D. Muller and W. Gessner, *Chemical Physics Letters,* 79:59–62, 1981).

Analysis of the coordination numbers in aluminum-oxygen compounds has revealed the aluminum coordination number patterns to be of three types: pure 4, pure 6, and compounds possessing both 4 and 6. Chemical-shift values for 6-coordination lie below 20 and usually below 10 ppm. Chemical shift values for 4-coordination lie between 60 and 85 ppm. Compounds possessing both classes of coordination exhibit two chemical shift peaks, one in each domain.

A study using a high-resolution solid-state NMR spectrophotometer was carried out to evaluate the aluminum coordination numbers of aluminum trihydroxide, sucralfate, and Compound III.

The spectra of aluminum trihydroxide and sucralfate were identical and possessed one peak at less than 3 ppm, revealing a pure 6-coordination number.

The spectra of Compound III:Al samples exhibited two chemical shift peaks, one at less than 3 ppm and the other at about 62 ppm, revealing a compound possessing both 6-coordination and 4-coordination.

The double peaks may indicate that the Compound III:Al samples are in fact a mixture, one of aluminum trihydroxide which is purely 6-coordinated, and a Compound III:Al type complex which is purely 4-coordinated.

Addition of alkali to a solution containing aluminum trichloride produces a precipitate of aluminum trihydroxide. The subsequent addition of 20 percent methanol by volume drives 98 percent of precipitated $Al(OH)_3$ back into solution. A conservative estimate by this method suggests that the contamination level of the Compound III:Al complex by aluminum trihydroxide could lie between 2 and 4 percent.

The technique of x-ray powder diffraction was used to study, respectively, the solid states of Compound III:Al, sucralfate and of aluminum trihydroxide. The x-ray spectra reveal that sucralfate and Compound III:Al are both amorphous solids, while aluminum trihydroxide exhibits the typical discrete peaks of a highly ordered crystalline solid. There is no evidence of the presence of this material in the Compound III:Al sample. Identification of the high trihydroxide peak at 32° allows one to assert that, by this method, such contamination could be identified if it were as low as 4 percent.

Therefore, Compound III:Al within the limits cited, is one pure substance.

Example 16: Study of the Dissolution and Buffering of Suspensions of Aluminum Trihydroxide, Sucralfate and Compound III:Al The serial addition of HCl to suspensions of aluminum trihydroxide, sucralfate and Compound III:Al reveals major differences between the titration curves and the buffering capacity, and therefore the structure of the solid state of these three entities. Thus, it takes 0.30 milliequivalents (meq) of HCl to reduce the pH value of drive 20 ml of distilled water from about pH 4.50 to below pH 2.00; from an initial pH of 4.44 it takes 0.90 meq HCl to effect the same change when the system contains 50 mg of aluminum trihydroxide; from an initial pH of 4.91 it takes 0.4 meq HCl if the system contains 50 mg sucralfate, and, from an initial pH of 4.23 it takes 1.2 meq if the system contains 50 mg of Compound III:Al (preparation 3).

| Relative Buffering Power between pH 4.5 and 2.0 | | |
|---|---|---|
| Sucralfate | Aluminum Trihydroxide | Compound III:Al |
| 1 | 6 | 11 |

From the above data it is clear that solid Compound III:Al exhibits a better dissolution-and-buffering action between pH 4.5 and 2.0 than either aluminum trihydroxide or sucralfate. These differences become important if one concedes that the consequences of such action can contribute to the anti-ulcer properties of the subject compounds.

Especially relevant to the question of Compound III:Al identity are the details of the dissolution-titration curves. Thus, whereas a principal apparent pK of aluminum trihydroxide is evident at pH 3.80, Compound III:Al exhibits no buffering power whatsoever at this pH value. In contrast, a principal apparent pK of Compound III:Al exists at pH 2.45. At this pH value aluminum trihydroxide exhibits only minor buffering power relative to distilled $H_2O$, but no pK. Sucralfate, in contrast to the other two compounds, exhibits only a minor buffering action between pH 1.73 and 1.47, which is small in comparison to actions of the other two compounds even in this pH region. Note that the term "apparent pK" in this context is meant to encompass the maximization of buffering that come both from solid-state dissolution and its titration as solute.

Certainly, then, the uniqueness of Compound III:Al is supported by the above data, as well as by the details of solubility in 20 percent methanol solution, as discussed above.

Note that another feature of Compound III:Al which distinguishes it from sucralfate is its relatively greater insolubility in acid. Although to the eye Compound III:Al and sucralfate are equally fine powders, with the addition of HCl, Compound III:Al goes into solution less readily than sucralfate. Although this can be seen throughout a titration, at pH 1.2 a suspension of 2.5 mg/ml Compound III:Al is still not all dissolved, whereas sucralfate achieves complete dissolution.

It is also noted that although Compound III:Al exhibits buffering power, Compound III, its precursor, exhibits no buffering power in the above pH range. This is compatible with the fact that the pK of Compound III is under pH 0.5. However, as discussed elsewhere Compound III also is able to prevent the perforation of established ulcers, and contributes a drug enhancement of ulcer capacity to maintain vascular integrity and prevent blood vessel obliteration, by clotting, in areas of tissue injury. Action of this type also contributes to the more intense anti-ulcer actions of Compound III:Al Example 17: 1,2-O-(2-Propylidene)-3,5,6-tri-O-sulfo-α-D-allofuranose, tripotassium salt (Compound VIII)

A solution of 1,2-O-(2-propylidene)-α-D-allofuranose (6.0 g. 27 mmol) in dry pyridine (60 mL) was vigorously stirred and cooled to −30° C. A solution of chlorosulfonic acid (11.2 g, 95 mmol) in chloroform (34 mL) was added dropwise while keeping the temperature of the reaction mixture between −30° C. and −15° C. After the addition was complete, the reaction mixture was allowed to gradually warm to ambient temperature over a time period of about 18 hours (overnight).

When analysis by TLC and paper electrophoresis indicated that sulfation was complete, the reaction mixture was cooled to −15° C. and a solution of water (10 mL) in pyridine (30 mL) was added dropwise with stirring at a rate sufficient to maintain the temperature below −15° C. The mixture was allowed to warm to ambient temperature after completing the addition, and was then concentrated under reduced pressure at 35° C. to light brown viscous oil.

To the resulting oil was added a 1M potassium hydroxide solution until a pH of 7 was measured. Water was then removed under reduced pressure at 35° C. to yield a beige solid.

The product was recrystallized twice from a methanol/water mixture to afford 5.5 g (35 percent) of a light beige crystalline solid: TLC $R_f$=0.3; M (glucose-6-sulfate)=1.6; decomposition point 190° C.; $^1$H NMR ($D_2O$), (chemical shifts relative to TMSPA) δ 5.85 (d, 1H), 4.91–4.87 (m, 1H), 4.85–4.79 (m, 1H), 4.78–4.70 (m, 1H), 4.43–4.33 (m, 1H), 4.24–4.14 (m, 2H), 1.50 (s, 3H), 1.31 (s, 3H). Analysis calculated for $C_9H_{13}K_3O_{15}S_3$: C, 18.81: H, 2.28; S, 16.74. Found: C, 18.42; H, 2.18; S, 15.73.

Example 18: 3,5,6-tri-O-sulfo-α-D-allofuranose, tripotassium salt (Compound IX)

A solution of 1,2-O-(2-propylidene)-3,5,6-tri-O-sulfo-α-D-allofuranose, tripotassium salt (Compound VIII; 1.1 g, 26 mmol) in 0.2M sulfuric acid (28 mL) was stirred and heated at 40° C. for 24 hours. Analysis of the reaction mixture by TLC and paper electrophoresis indicated that hydrolysis was complete.

The reaction mixture was permitted to cool to ambient temperature and was then neutralized to pH 7 by the portionwise addition of a saturated barium hydroxide solution. The precipitate that formed was removed by filtration and the solution was concentrated under reduced pressure to one-half of its original volume. Additional precipitate that had formed was removed by filtration. Carbon dioxide was then added to the filtrate and the precipitate that formed during this process was also removed by filtration. The resulting filtrate was concentrated under-reduced pressure to leave a brown oil.

The product was applied to an ion exchange column, prepared using Dowex 50X8-200 ($H^+$ form) ion exchange resin. Following elution with water, the fractions containing the desired product were combined and neutralized to pH 7 by adding 1M potassium hydroxide solution. The solvent was then removed under reduced pressure.

The product was dissolved in the minimum quantity of water and methanol was added gradually. The purified potassium salt of the trisulfate was precipitated as an amorphous beige powder, 0.6 g (57 percent): TLC $R_f$=0.2; M (glucose-6-sulfate)=$^1$H NMR ($D_2O$, chemical shifts relative to TMSPA) δ 5.43 (d, 1H), 5.02–4.96 (m, 1H), 4.86–4.45 (m, 2H), 4.40–4.10 (m, 3H). Analysis calculated for $C_6H_9K_3O_{15}S_3$: C, 13.48; H, 1.70; S, 17.99. Found: C, 13.04; H, 1.72; S, 14.83.

Example 19: Inhibition of Gastric Ulcers Induced by Ethanol Alone and by Ethanol with Heparin In the presence of stress, heparin has been found to provoke a delayed and significant tendency to cause bleeding from vulnerable organs, due to an adverse effect on vascular endothelium, long after its anticoagulant action has dissipated (Jaques, *Chest,* 88:751, 1985).

This non-anticoagulant action of heparin has been used to develop a method that provokes the bleeding ulcer phenomenon, so that its possible control by a drug can be studied. In this method, a relatively large amount of ethanol is administered to rats by oral gavage (1.0 ml/200 gm), a procedure widely used to produce ordinary gastric ulceration. This injection, however, is given in combination with the intraperitoneal injection of heparin sulfate (10 mg/kg). Ethanol or heparin, when administered alone, as above, do not produce hemorrhage from focal gastric ulcers. Given together they do cause bleeding after 17 and before 24 hours following their combined administration. This phenomenon has nothing to do with failed blood coagulation, since coagulation time becomes normal by six hours after heparin injection at 10–20 mg/kg.

Compound III inhibits both the ulcer and the bleeding phenomena. The results of a typical study are shown below where group numbers of animals studied (n) was between 9 and 13. Compound III treatment was 50 mg/kg by oral garage in distilled water as diluent, at 45 minutes before ulcer induction.

The effects of ethanol alone and ethanol plus Compound III were assessed four hours after ethanol administration. The effects of ethanol plus heparin and ethanol plus heparin plus Compound III were assessed 24 hours after administration of the ulcer inducing combination. Ulcer formation was assessed as discussed in Example 20.

In this and the following examples, the potassium salt of the drug indicated by a Roman numeral was used; i.e., M is potassium ($K^+$).

| | Frequency of Ulcer-Bearing Rats, as Percent of Total in Group | |
|---|---|---|
| Groups | A Ulcers | B Bleeding Ulcers |
| A. Ethanol Only | 56 | 0 |
| Ethanol + Compound III | 11 | 0 |

-continued

| Groups | Frequency of Ulcer-Bearing Rats, as Percent of Total in Group A Ulcers | B Bleeding Ulcers |
|---|---|---|
| B. Ethanol + Heparin | 85 | 62 |
| Ethanol + Heparin + Compound III | 25 | 0 |

Chi square analysis: Compound III inhibits the formation of ulcers without regard to type; when control (ulcer-induced) and drug-treated groups from Sections A and B are combined, $P<0.01$.

Compound III inhibits bleeding ulcer formation, $P<0.01$.

Example 20: Development of Gastric Pathology Following Inflammatory Stress and Indomethacin: its Suppression by Compound III Stress was induced by the following procedure. On day one, under ether anesthesia, 18 male Sprague Dawley rats were injected with a suspension of Zymosan A (1 mg/ml in normal saline; Sigma Chemical Co.) in each hind paw. Swelling developed and persisted. This treatment generated activated blood complement locally (including the C5a moiety), which then spread by the bloodstream throughout the animal. In the hind feet, the treatment induced local persistent inflammation and discomfort, and contributed to the development of gastric pathology at a distance.

Twenty-four hours later all rat paws were reinjected, this time with 0.1 ml of proinflammatory zymosan-activated rat serum containing additional amounts of inflammatory complement fragment C5a (as in Example 23, hereinafter). Five hours later 30 mg/kg indomethacin in an aqueous suspension was given to nine such rats by oral garage. These rats also received a subcutaneous injection of 0.1 ml normal saline. Nine other such rats were given indomethacin as above, and Compound III (50 mg/kg in normal saline subcutaneously). Four additional rats, not stressed (normal) were given water by garage as a placebo and saline subcutaneously. All rats were fed ad libitum on standard diet.

Twenty-four hours later all animals were sacrificed by ether euthanasia. Their stomachs were washed with saline and evaluated for ulcer-related pathology using an illuminated magnifying glass. This assay is similar to that reported by Kinney et al., *J. Med. Chem.*, 33:327 (1990). Separately, the stress and indomethacin induced no ulceration.

Results

Rat Stomachs—Normal

1) Supple; endothelium is satin-smooth, pink.
2) Supple; endothelium is satin-smooth, pink.
3) Supple; endothelium is satin-smooth, pink.
4) Supple; endothelium is satin-smooth, pink.

Rat Stomachs—Stress + Indomethacin

1) Relatively rigid and ridged; endothelium is dry, gritty and pale yellow. No ulceration. Pathology score: 0.5.
2) Appearance as #1; one circular ulcer. Pathology score: 1.0.
3) Appearance as normal stomach. No ulceration. Pathology score: 0.0.
4) Appearance as normal stomach. No ulceration. Pathology score: 0.0.
5) Appearance as #1: one ulcer with clotted blood in and adjacent to opening in mucosa. Pathology score: 4.0.
6) Appearance as #1; one perforated ulcer, ringed with clotted blood. Pathology score: 7.0.
7) Appearance as #1; no ulceration. Pathology score: 0.5.
8) Appearance as #1; no ulceration. Pathology score: 0.5.
9) Appearance as #1; no ulceration. Pathology score: 0.5.

Mean Pathology score: 1.43

Rat Stomachs—Stress + Indomethacin + Compound III

1) Supple; endothelium is satin-smooth, pink. Pathology score: 0.0.
2) Supple; endothelium is satin-smooth, pink. Pathology score: 0.0.
3) Supple; endothelium is satin-smooth, pink. Pathology score: 0.0.
4) Supple; endothelium is satin-smooth, pink. Pathology score: 0.0.
5) Supple; endothelium is satin-smooth, pink. Pathology score: 0.0.
6) Supple; endothelium is satin-smooth, pink. Pathology score: 0.0.
7) Supple; endothelium is satin-smooth, pink. Pathology score: 0.0.
8) Supple; endothelium is satin-smooth, pink. Pathology score: 0.0.
9) Supple; endothelium is satin-smooth, pink. Pathology score: 0.0.

Mean Pathology score: 0.00.

It is seen that use of a compound of this invention can inhibit ulceration and pre-ulcerative stomach pathology caused by stress and a typical NSAID, indomethacin. Thus, indomethacin and similarly acting NSAIDs can be more safely administered for their usual anti-inflammatory and pain killing effects when co-administered with a compound of this invention.

Example 21: Further Study of Development of Gastric Pathology Following Inflammatory Stress and Indomethacin: its Suppression by Compound III In contrast to the study of Example 20, above, in this study animals were food deprived for 24 hours before and also during the 24 hours following drug treatments. All animals were subjected to the inflammatory stress as described in Example 20. Eight such rats received 30 mg/kg indomethacin, and eight rats received indomethacin and Compound III (subcut., 50 mg/kg). Four rats, not stressed, were given placebo by garage.

All animals were sacrificed by ether euthanasia 24 hours later, and their stomachs evaluated for ulcer-related pathology.

Results

In the stressed animals given indomethacin alone, pathology was much more severe than in Example 20. For scoring, therefore, the frequency of ulcers per rat stomach was quantified, and whether they were or were not bleeding.

In the group given indomethacin alone, all eight rats had 1–5 ulcers. Of a total of 23 ulcers found in this group, 22 were bleeding. In the group given indomethacin and also treated with Compound III, only two rats had two and three ulcers, respectively. None were bleeding.

| Group | Per Rat Total Ulcer Frequency n ± SE | Bleeding Ulcer Frequency Mn ± SE |
|---|---|---|
| Indomethacin | 2.88 ± 0.67 | 2.65 ± 0.063 |
| Indomethacin + Compound III | 0.63 ± 0.42 | 0.00 |

Statistical analysis by Student's t test:
Total ulcers: indomethacin + Compound III < indomethacin alone P<0.01;
Bleeding ulcers: indomethacin + Compound III < indomethacin alone, P<0.001.

This study again illustrates the ulcer-producing effect of indomethacin and the striking capacity of a compound of this invention to suppress this undesirable side effect of indomethacin when administered along therewith.

Example 22: Inhibition of the Injury of Organ Ischemia (Depressed Organ Blood Flow, Producing Oxygen Lack)

This important disease model is used to evaluate aspects of tissue injury that occur in heart attack, or myocardial infarction, and stroke. Under these conditions, a significant period of injury can occur after blood flow has been restored, during the period of reperfusion. In this period, injury results from attack by superoxide and related redox-active compounds and free radicals. To evaluate the effect of drugs of the invention on damaging events in this period, ischemia of the rat paw was induced according to the method of Oyanagui, *Free Radical Research Communications,* 4:385, (1988), and was treated as discussed below.

To produce ischemia, blood flow to the left hind foot was largely interrupted by application of a tourniquet made up of two size 18 rubber bands wound eight times around the leg just behind the heel. This tourniquet was left in place for 45 minutes and then removed. Both application and removal of tourniquet were carried out under ether anesthesia. Injury was equated with organ swelling, which was assayed by measurement of the dorsoventral foot diameter with a Schnelltaster caliper, just before application of the tourniquet and at various times following tourniquet removal, during the reperfusion period.

Superoxide dismutases, free radical scavengers and the xanthine oxidase inhibitor allopurinol suppress the edema that develops following removal of the tourniquet. Dexamethasone is effective only when administered more than three hours in advance. Nonsteroidal anti-inflammatory drugs, such as indomethacin or diclofenac, are not effective at any time. In contrast, compounds of this invention inhibit the edema produced by this form of ischemia, when administered within one hour of induction, as discussed hereinafter.

Rats employed were Sprague Dawley males, weighing 240–280 grams. Drug comparisons were made here employing measurements 30 minutes into the reperfusion period. The widely studied drug allopurinol, a xanthine oxidase inhibitor and a free radical scavenging agent, used in the treatment of gout, and widely used to suppress experimental post-ischemic reperfusion injury was used as an experimental treatment standard. In studies below, allopurinol and all new drugs were given intraperitoneally 45–60 minutes prior to application of the tourniquet. Data are reported as the mean swelling (Mn)±standard error (SE). The control for each group was the observed swelling without drug treatment, whereas the indicated drug treatment data were obtained by causing the ischemia plus treatment with the indicated drug. Group n is 5 or 6.

| | Post-Ischemic Reperfusion 30 Minute Paw Swelling (0.1 mm, Mn ± SE) | Swelling Change as a Result of Treatment |
|---|---|---|
| A. Control | 12.7 ± 0.98 | |
| Compound III (0.2 mg/kg) | 6.0 ± 0.32 | −53% |
| B. Control | 20.5 ± 0.76 | |
| Compound III (0.2 mg/kg) | 12.2 ± 0.70 | −40% |
| Allopurinol (20 mg/kg) | 13.3 ± 0.56 | −35% |
| C. Control | 18.4 ± 0.54 | |
| Compound III (0.2 mg/kg) | 10.2 ± 0.28 | −45% |
| Compound VI (0.2 mg/kg) | 9.1 ± 0.27 | −50% |
| D. Control | 11.4 ± 0.51 | |
| Compound IV (0.2 mg/kg) | 21.2 ± 2.25 | +86%* |

*edema enhancement
All of the above drug effects are significant by Student's t test at levels of P < 0.02.

In another study, drug comparisons were made at various times after the reperfusion period. In this study, control and drug treatment groups were as above. All drugs were administered intraperitoneally 45 minutes prior to application of the tourniquet.

| Group | Reperfusion Time (Mins.) | Paw Swelling (0.1 mm, Mean ± SE) | % Change as a Result of Treatment |
|---|---|---|---|
| Control | 20 | 8.20 ± 1.02 | |
| | 30 | 6.60 ± 0.87 | |
| Compound III | 20 | 4.60 ± 0.40 | −46 |
| | 30 | 4.20 ± 0.37 | −36 |
| Compound VIII | 20 | 4.60 ± 0.40 | −46 |
| | 30 | 2.40 ± 0.51 | −64 |

Statistical analysis by Student's t test at 20 minutes showed Compound III > Control significant at p<0.02 and Compound VIII > Central significant at p<0.005; at 30 minutes, Compound III > Control significant at p < 0.05 and Compound VIII > Control significant at p < 0.01.

At 45 minutes and 60 minutes of reperfusion time, paw swelling in control and Compound III groups began to converge as the paws returned to their pre-ischemic size. However, the paw swelling of Compound VIII treated animals and controls converged much more slowly. The paw swelling of Compound VIII-treated animals was 71 percent less than control at 60 minutes of reperfusion time.

In subsequent studies, in which the oral treatment route was employed, Compound III inhibited ischemic rat paw edema by 44 percent after 20 minutes.

Neutrophils, as determined by the myeloperoxidase assay (MPO), did not enter the paw during this form of edema; i.e., MPO values for normals, ischemic and drug-treated ischemic paws were not different from each other, in contrast to the ZAS-produced edema discussed hereinafter.

Example 23: Injury Provoked by Zymosan-Activated Serum: Its Relation to Polymorphonuclear Cell Accumulation Zymosan is a complex yeast cell wall polysaccharide that activates blood complement by the indirect route, generating inflammatory polypeptides such as C5a, a so-called "bugle call" protein, that is highly chemotactic for neutrophils. The contributing and causative role for neutrophils in the development of stroke and in the pathology that occurs in the reperfusion period following clot-lysis in myocardial infarction has been the subject of intensive research for the last several years, Lucchesi, *Ann. Rev. Physiol,*, 51:561, (1980).

For the present studies, zymosan-activated serum (ZAS) was made by incubating reconstituted lyophilized rat serum with 10 mg/ml zymosan A for one hour at 37° C., and then microfiltering to remove the zymosan.

In the first study, distilled water vehicle or 50 mg/kg Compound III in water were given by oral gavage to 9 control and 9 drug-treated adult male rats, respectively, and 90 minutes later the dorsoventral diameter of the hind feet were determined by Schnelltaster caliper. Sera [0.1 ml ZAS or 0.1 ml normal serum (NS)] were thereafter injected into opposite hind paws of the same rat under ether anesthesia. Below are given the paw swellings that developed at 2 and 3 hours, in response to ZAS and to normal serum, in the absence and presence of drug treatment. Data are reported previously.

| | Paw Swelling (0.1 mm) | | |
|---|---|---|---|
| Hour post- | ZAS | ZAS + Compound III | Swelling Change |
| 2 | 27.22 ± 1.97 | 10.78 ± 1.94 | −60% |
| 3 | 28.89 ± 2.48 | 16.11 ± 2.94 | −44% |
| | NS | NS + Compound III | |
| 2 | 11.22 ± 1.28 | 7.67 ± 1.41 | −32% |
| 3 | 11.44 ± 1.55 | 9.44 ± 1.28 | −17% |

By Student's t test, drug inhibition of ZAS-induced inflammation is significant at levels of $P < 0.01$.

The relationship of neutrophil infiltration to ZAS-induced swelling, and its drug-inhibition, was evaluated in another study. In this study, all procedures employing ZAS and Compound III were carried out as above, except that, Compound III was administered 45 minutes before ZAS, and standardized samples of the swollen footpads were removed and subjected to analysis for myeloperoxidase activity (MPO), according to the method of Lundberg et al., *Inflammation,* 7:247, (1983). MPO is a neutrophil-specific enzyme, and its assay is the most widely used method of identifying the degree of neutrophil participation in organ pathology.

| Group | Paw Swelling (0.1 mm) | MPO (Rel. Units) |
|---|---|---|
| Normal (Untreated) (n = 6) | — | 11.67 ± 1.87 |
| ZAS alone (n = 12) | 34.58 ± 2.45 | 94.42 ± 12.81 |
| ZAS + Compound III (17 mg/kg) (n = 6) | 16.83 ± 2.12 | 32.17 ± 2.83 |
| ZAS + Compound III (50 mg/kg) (n = 12) | 15.25 ± 3.99 | 41.67 ± 8.93 |

Drug inhibitions of paw swelling and MPO accumulation are highly significant by Student's t test, all at levels of $P < 0.01$.

Example 24: In Vitro Neutrophil Chemotaxis

In vitro neutrophil chemotaxis studies were carried out by standard methods, as follows:

Mice were injected with complete Freund's adjuvant (CFA) and peritoneal cells, principally neutrophjls (>90 percent), were reproved from the mice 24 hours thereafter. Blind-well chemotactic chambers (Nucleopore Corp., Pleasanton, Calif.) were utilized.

Medium (RPMI 1640 plus 10 percent fetal calf serum) or medium plus 20 percent zymosan-activated rat serum (ZAS) was added to the lower compartment of each chamber. A nucleopore filter (8 μm pore size) was placed between compartments and $1\times10^5$ peritoneal neutrophils (above) suspended in medium were placed in the upper compartment. Chambers were incubated for six hours, after which time the filters were removed and stained with Giemsa stain. The number of cells on the lower surface of the filter was counted under a microscope. Treatment groups were assayed in duplicate.

The studies were carried out more specifically as follows:

Zymosan (Sigma Chemical Co., St. Louis, Mo.) was mixed with rat serum for one hour at 37° C. at 1 milligram (mg)/ml. The resulting chemoattractant composition was filtered, aliquotted and stored frozen at −70° C. prior to use.

The above chemoattractant composition was used as a 20 percent v/v solution in medium.

The chemotaxis chambers were arranged as follows:

| Chamber # | Bottom | Top |
|---|---|---|
| 1-2 | medium | cells (0.1 ml) + medium (0.1 ml) |
| 3-4 | chemoattractant | cells (0.1 ml) + medium (0.1 m.) |
| 5-6 | chemoattractant | cells (0.1 ml) + drug (0.1 ml) |
| 7-8 | chemoattractant | cells (0.1 m.) + drug (0.1 ml) |

The chambers were incubated at 37° C. for six hours, after which the chambers were dismantled, and the filters removed and treated as follows:

a) The filters were immersed in Giemsa stain diluted 1:50 for 30–45 minutes.

b) The stained filters were rinsed gently in distilled water for 3–5 minutes.

c) The stained, rinsed filters were air dried without blotting.

Several compounds described herein and control compounds ("drug", above) were examined at various concentrations, in duplicate. The molar concentration of a drug that inhibited the observed chemotaxis by 50 percent, defined as the $ID_{50}$ value, was determined as shown below.

| Drug | $ID_{50}$ (M) |
|---|---|
| Compound II | $3 \times 10^{-5}$ |
| Compound III | $2 \times 10^{-7}$ |
| Compound IV | $>1\times 10^{-5}$ |
| Compound V | $2 \times 10^{-6}$ |
| Compound VI | $1 \times 10^{-6}$ |
| Compound VII | $<1 \times 10^{-4}$ |
| Probenecid | $3 \times 10^{-6}$ |
| SITS* | $>2 \times 10^{-5}$ |
| Ibuprofen | $>5 \times 10^{-5}$ |
| Prednisone | $>>5 \times 10^{-5}$ |
| $PGE_2$** | $1 \times 10^{-7}$ |

*SITS = 4-Acetamido-4'-isotheiocyano-stilbene-2,2'disulfonate
**$PGE_2$ = Prostaglandin $E_2$ Data from nine separate studies are shown below.

| Study Number | Drug | Dose (μg/ml) | Percent Inhibition |
|---|---|---|---|
| I | Compound III | 100.0 | 68.0 |
| | | 200.0 | 60.0 |
| II | Compound III | 0.1 | 55.0 |
| | | 1.0 | 69.0 |
| | | 10.0 | 87.0 |
| | | 100.0 | 80.5 |
| III | Compound III | 0.1 | 47.0 |
| | | 1.0 | 65.0 |
| | | 10.0 | 76.0 |
| | Compound IV | 0.1 | 24.0 |
| | | 1.0 | 44.0 |
| | | 10.0 | −26.5 |
| | Compound VI | 0.1 | 21.0 |
| | | 1.0 | 44.0 |
| | | 10.0 | 85.0 |
| IV | Compound III | 0.1 | 68.5 |
| | | 1.0 | 90.0 |
| | | 10.0 | 92.5 |
| | Compound IV | 0.1 | 4.5 |
| | | 1.0 | 28.5 |
| | | 10.0 | −52.5 |
| | Compound VI | 0.1 | −12.0 |
| | | 1.0 | 47.0 |
| | | 10.0 | 85.0 |
| V | Compound III | 0.1 | 70.0 |
| | | 1.0 | 88.5 |
| | | 10.0 | 97.5 |
| | Compound V | 0.1 | −8.0 |
| | | 1.0 | 62.0 |
| | | 10.0 | 101.0 |
| | Probenecid | 0.1 | 5.5 |
| | | 1.0 | 59.5 |
| | | 10.0 | 89.5 |
| VI | Compound III | 0.1 | 77.0 |
| | Compound VII | 0.1 | 8.0 |
| | | 1.0 | 23.0 |
| | | 10.0 | 29.0 |
| | Compound II | 0.1 | 2.5 |
| | | 1.0 | 45.5 |
| | | 10.0 | 48.5 |
| | SITS | 0.1 | 18.5 |
| | | 1.0 | −12.5 |
| | | 10.0 | 48.5 |
| VII | Compound III | 0.1 | 47.5 |
| | | 1.0 | 77.0 |
| | | 10.0 | 87.0 |
| | Ibuprofen | 0.1 | 17.5 |
| | | 1.0 | 9.3 |
| | | 10.0 | 35.5 |
| | Prednisone | 0.1 | 15.5 |
| | | 1.0 | 16.0 |
| | | 10.0 | 20.0 |
| VIII | Compound III | 0.01 | 1.5 |
| | | 0.1 | 38.0 |
| | | 1.0 | 63.5 |
| | | 10.0 | 74.5 |
| | $PGE_2$ | 0.2 | 71.5 |
| IX | Compound III | 0.1 | 43.0 |
| | | 1.0 | 70.0 |
| | $PGE_2$ | 0.01 | 71.0 |
| | | 0.1 | 91.5 |
| | $PGE_2$ (0.1) + | 0.1 | 73.5 |
| | Compound III | 1.0 | 77.5 |
| | $PGE_2$ (0.1) + | 0.1 | 93.5 |
| | Compound III | 1.0 | 85.0 |

The above data are uncorrected for the average small degree of non-attractant-induced cell migration.

The above data illustrate that at about 10 μg/ml, attractant-induced chemotaxis fell in the range of about 75–90 percent for Compound III. That compound was also about 2–3 orders of magnitude (about 100–1000) times as potent as ibuprofen and prednisone.

By microscopic examination, Compound VI was observed to exhibit a diffuse toxic granularity in the cells. By similar study, probenecid treatment caused a stringy, elongated deformation in the neutrophils. The above were the only expressions of cytotoxicity observed to affect the neutrophils in this study.

Example 25: Inflammation Provoked by Carrageenan Injection

Carrageenan is a complex sulfated polysaccharide derived from Irish moss. It is the most classic acute inflammation inducer used in pharmacology, and anti-inflammatory effects of aspirin-like drugs against carrageenan edema in laboratory animals are predictive of their order of potency in arthritis in man.

In this study employing mice, anti-inflammatory effects of Compound III were compared to those of the free radical-inhibiting enzyme superoxide dismutase (SOD). Treatments were given intravenously (IV) for SOD, and IV and intraperitoneally (IP) for Compound III, 45 minutes after injection of 150 μg carrageenan (in saline) per foot pad. To assess swelling, foot pad dorsoventral diameters were measured at zero time and two hours after carrageenan injection.

| | Foot-Pad Swelling (0.1 mm) | Swelling Change |
|---|---|---|
| Control (n = 8) | 3.8 ± 0.67 | |
| SOD (100 units) (n = 8) | 1.55 ± 0.31 | −51% |
| Compound III (50 mg/kg IV + 50 mg/kg IP) (n = 8) | 0.82 ± 0.46 | −74% |

Ibuprofen (50 mg/kg subcutaneously) and Compound III (30 mg/kg subcutaneously) provided 24 and 26 percent reductions in swelling, respectively, neither of which reductions was significant in a Student's t test.

Example 26: Development of Gastric Ulcers in Rats with Corona Virus Infection, and Treated with Indomethacin: its Suppression by Compound III and the Anti-Ulcer Drug Cimetidine Corona virus is a non-lethal upper respiratory viral pathogen that not infrequently infects rat colonies. It is a type of rodent coryza or catarrh, the equivalent of a disease that falls somewhere between human influenza and a severe common cold. The animals of this study suffered from this condition, a circumstance which was evident by observation, and which was confirmed by virological diagnosis at the Biological Resources Laboratory of the University of Illinois at Chicago. Since stress is a common component of peptic ulcer development in both animals and man, it was concluded that this feature of the status of these experimental animals rendered them appropriate for an ulcer study.

In this study, animals were not food deprived and were divided into treatment groups such that 15 rats received 30 mg/kg indomethacin alone (in water by oral gavage), 14 rats received indomethacin plus an injection of 25 mg/kg cimetidine subcutaneously, and 7 rats received indomethacin plus subcutaneous injection of 17.5 mg/kg of Compound III.

All animals were sacrificed by ether euthanasia 24 hours later and their stomachs evaluated for ulcer pathology. In this study ulcers were not hemorrhagic. Results are shown below as the average number of stomach ulcers per stomach.

| Treatment Group | Per Stomach Ulcer Frequency Mn ± SE | Percent Inhibition |
|---|---|---|
| Indomethacin | 2.53 ± 0.52 | — |
| Indomethacin + cimetidine | 1.07 ± 0.25 | 58 |
| Indomethacin + Compound III | 0.86 ± 0.46 | 66 |

The above results show that the average ulcer frequency is about 2.5 ulcers/per rat in the control group. Cimetidine in the dose given reduces this frequency by 58 percent, whereas Compound III, in the dose given reduces ulcer frequency by 66 percent. Both drug effects are statistically significant, at P<0.02.

Example 27: Effect on Established Adjuvant Arthritis

Adjuvant arthritis was studied because it allows gaining of insight into effects of a drug in established and chronic inflammatory disease. Adjuvant arthritis shares certain features with rheumatoid arthritis but it is distinct. It is widely used in industry because it allows one to predict the potency of non-steroidal anti-inflammatory drugs (NSAID's) [Weichman, in *Pharmaceutical Methods in the Control of Inflammation,* Chang et al., eds.; Alan R. Liss, New York (1989) p. 362].

The rats used were of the Lewis strain, especially vulnerable to disease induction. Chronic polyarthritis was induced by the subcutaneous injection of complete Freund's adjuvant (CFA) into the rat tail. The CFA employed consists of 10 mg/ml heat-killed tubercle bacilli suspended in paraffin oil. An amount of 0.1 ml was injected, and the disease was allowed to develop over 14 days before daily assessments were made and treatments were initiated. Measurements that assess both increase in hind paw joint swelling and loss in hind limb function are taken.

Indomethacin was employed as a reference standard and given at 2 or 5 mg/kg. Treatment effects of Compound III, alone at 50 mg/kg given by oral gavage and in combination with indomethacin were assessed. Compound III was dissolved in water and indomethacin was suspended in water by homogenization. Both were administered sequentially by oral gavage.

Measurements by caliper include the lateral diameter of the ankle joint of each hind limb, and the dorsoventral diameter of the foot, just behind the toes. The prime measurement of function focusses on the fact that in many animals by day 14, and in most animals by day 16 after adjuvant administration, the arthritic rat can lose use of his hind limbs, which then are dragged behind him like logs. To quantify the recovery of function during treatment, a technique of Martel et al., *Agents Actions,* 15:403 (1984) was adapted. A blind assessment of the number of animals in each group that were able to draw their leg(s) under them and have these bear weight was carried out. The data obtained are listed in the tables below.

HIND-FOOT MOBILITY IN ADJUVANT ARTHRITIS
Total Immobility - Percent and Frequency[a]

| Day | Indo-5[b] | Indo-5[b] + Compound III | Control |
|---|---|---|---|
| 0 | 100 (10/10) | 100 (10/10) | |
| 1 | 70 (7/10)** | 10 (1/10)** | |
| 2 | 20 (2/10) | 10 (1/10) | |
| 3 | 10 (1/10) | 10 (1/10) | 100 (12/12) |

-continued

HIND-FOOT MOBILITY IN ADJUVANT ARTHRITIS
Total Immobility - Percent and Frequency[a]

| Day | Indo-2[c] | Indo-2[c] + Compound III |
|---|---|---|
| 0 | 100 (9/9) | 100 (14/14) |
| 1 | 67 (6/9)* | 67 (6/9)* |
| 2 | 44 (4/9)** | 0 (0/14)** |
| 3 | 44 (4/9) | 14 (2/14) |

[a]Percentage of animals exhibiting total immobility is shown first, with the frequency shown in parenthesis.
[b]Indo-5 = indomethacin at 5 mg/kg/day.
[c]Indo-2 = indomethacin at 2 mg/kg/day.
By Chi-square analysis: Indo-2 > Indo + Compound III
*$p < 0.02$
**$p < 0.01$ Example 28: Generalized Schwartzmann Reaction in the Rabbit The Generalized Schwartzmann Reaction (GSR) is a pathology in which two intravenous injections of non-lethal amounts of bacterial endotoxin, when separated by 8 to 36 hours, promote thrombotic and tissue-destructive processes in the lung, producing disseminated pulmonary thrombosis and necrosis in otherwise untreated rabbits. The pathology in question has been found to be in large part a consequence of the behavior of activated neutrophils [Niemetz et al., *Nature London New Biol.,* 232:247 (1971)].

A. In this study, eight six-week old salmonella-free male rabbits each weighing about 1.5 kg were injected IV with saline vehicle and eight similar rabbits were injected IV with 50 mg/kg of Compound III in the same vehicle. One hour later, all of the animals were injected IV with 100 μg of *E. coli* lipopolysaccharide (LPS; Sigma Chemical Co.) on day one and with the same amount of LPS on day two, twenty hours later. Animals were evaluated for clinical signs at 24 and 48 hours, and were sacrificed for organ evaluation 48 hours after the second endotoxin injection.

In assessing gross pathology, separate scores were developed in four categories and these were then summed and added, in one instance, to a score for clinical signs.

Gross Pathology Categories (1) Surface redness, diffuse or mottled (reflecting hyperemia, hemostasis). +2 to +4.

(2) Discrete focal surface lesions (reflecting thrombosis without disruption of gross pulmonary architecture).

| | |
|---|---|
| 1-6 mm | +1 |
| 7-12 mm | +2 |
| 13-20 mm | +3 |

(2a) Gross lung destruction

| | | |
|---|---|---|
| Add: | 1-6 mm | +2 |
| | 7-12 mm | +4 |

(3) Diffuse petechia, affecting all lobes +6

| Clinical Signs | | |
|---|---|---|
| Rales | +2 | (In fact, present in only one untreated animal) |
| Diarrhea | +2 | (Usually a pre-shock response to higher dosage of endotoxin, evident in none.) |

-continued

Results- Stigma of categories #2-3, contributed prominently to the pathology of the control group.

|  | Mean Pathology Score | Drug Effect |
| --- | --- | --- |
| Untreated | 8.00 ± 1.02 | — |
| Compound III | 2.25 ± 1.10 | −72% |
|  |  | P < 0.01 |

B. Employing the same batch of endotoxin, the same induction methodology was applied to an older, seven month old group of rabbits. These animals did not develop GSR, but proved far more sensitive to the systemic toxic effects of the bacterial lipopolysaccharide than the younger animals studied above, as revealed by the preshock signs: diarrhea and malaise. In this study the treatment group received 10 mg/kg of Compound III, given IV, as above.

After one endotoxin injection, at 24 hours, half, and after two endotoxin injections, at 48 hours, all eight control animals exhibited prominent diarrhea and some degree of malaise, as evinced by lowered ears and splayed front feet. In contrast, only one of eight Compound III-treated rabbits exhibited these symptoms of early shock, by 48 hours.

These data exhibited a high statistical significance by Chi Square analysis, with regard to diarrhea frequency: P<0.01.

Example 29: Toxicology Studies
  A. Acute Toxicity in the Mouse

Acute intraperitoneal and oral toxicity of Compound III was studied in the mouse. Ten animals per dose were employed.

The intraperitoneal $LD_{50}$ of Compound III in normal saline was 2.8 g/kg. However, 3.0 g/kg gave no toxicity by the intravenous route. Nor was oral death produced by the highest dose employed, 4.5 g/kg, in water.

B. Chronic Toxicity in C57 Black Rats

C57 Black mice were employed in a study of tumor metastasis, that failed in its intended purpose because the injected tumor cells did not take. However, eight mice were treated with Compound III by drinking water, for a period of 28 days. During this time, the average daily dose consumed was 175 mg/kg. At termination the treated animals weighed as much as the controls, and looked sleeker, because of an anecdotally documented absence of fighting.

Example 30: Effect on Gastric Submucosal Thrombi

Thrombosis was induced in rat stomach submucosal blood vessels by the following two-step treatment. First, 1.5 ml of 100 percent ethanol was administered by oral gavage. This produces non-specific injury to tissues and blood vessels of the gastric mucosa. Second, 1.0 mg of adenosine diphosphate (ADP) in 1.0 ml of $H_2O$, was administered by oral garage 15 minutes after the administration of ethanol. Administration of ADP biases the organ response towards thrombosis by inducing platelet aggregation.

The pathology generated is typically a disseminated pattern of multiple small thrombi, observed on examination of the gastric mucosa, 1-3 hours after ethanol administration. These thrombi are dark red, dilated, thrombosed submucosal blood vessel segments, each being approximately 1 mm thick and 2 to 6 mm long. Under control conditions ethanol induces these stigma with a frequency of 0-13 per stomach; their average frequency of appearance is increased by about 50 percent, and the frequency of stomachs exhibiting 13 or more submucosal thrombi increases five-fold with the use of the platelet activator, ADP.

In these studies, animals were treated with drug or centrol at one hour prior to ethanol administration. Thrombosis was induced as discussed before, and animals were sacrificed at 1.5 hours after ethanol administration. Focal thrombi were then counted. In this study, n=9-10.

| Inhibition of Gastric Submucosal Thrombi | | |
| --- | --- | --- |
|  | Mean Thrombi per Stomach, ±SE | Drug Effect % |
| 1) Control | 10.60 ± 1.42 |  |
| 2) Compound III 10 mg/kg IV | 4.00 ± 1.12 | −62.3 |
| 3) Compound VIII, 10 mg/kg IV | 6.56 ± 1.60 | −38.1 |

Example 31: Blood Coagulation Study
  A. In Vitro Study

Heparin and dextran sulfate are noted for their activity in inhibiting blood coagulation. To assess the effect on coagulation, if any, of a compound of the invention, a comparative evaluation was made using mouse blood.

Heparin at 10 µg/ml in normal saline, Compound III at 10 µg/ml in normal saline and normal saline were placed in separate tubes. One ml of freshly drawn mouse blood was added to each tube, and the tube contents were mixed. The clotting time was then noted for each tube, and the results are as shown below:

| Assay Group | Mouse No. | Clotting time (minutes) | Average clotting time |
| --- | --- | --- | --- |
| Control | 1 | 5.0 | 4.33 ± 1.20 |
|  | 2 | 2.0 |  |
|  | 3 | 6.0 |  |
| Heparin | 1 | >60 | >60 |
|  | 2 | >60 |  |
|  | 3 | >60 |  |
| Compound III | 1 | 2.0 | 2.0 ± 0.71 |
|  | 2 | 1.0 |  |
|  | 3 | 4.0 |  |
|  | 4 | 1.0 |  |

As can be seen from the above data, heparin had a profound effect upon the coagulation time by making the blood uncoagulatable after 60 minutes, whereas a compound of the invention did not prolong the coagulation time. P<0.001.

B. In Vivo Study

A study of mouse tail bleeding time, which is an in vivo model of platelet aggregation and thrombosis was also conducted. In this widely employed model, bleeding was induced by a standardized transection of the tail tip and subsequent bleeding time was determined after vertical immersion of the tails in isotonic saline at 37° C. for thirty seconds. Compound III more than doubled bleeding time (P<0.05, drug doses of 50 mg/kg and 150 mg/kg administered subcutaneously) and was equipotent with aspirin (75 mg/kg IP), indicating that each was equivalently interfering with the aggregation of platelets. Orally administered Compound III was also found to be about equipotent with aspirin in prolonging mouse tail bleeding time.

Two compounds of the invention, Compound III and Compound VIII, were assessed as compared with aspirin, in another study of mouse tail bleeding time. In this study, the mice were housed in a standard animal room rather than in a noisy small animal isolator. Also, all three drugs were administered by an intraperitoneal route, rather than a subcutaneous route for Compound III and an intraperitoneal route for aspirin.

In this study, both Compound III and Compound VIII were more effective than aspirin in prolonging mouse tail bleeding time.

| Treatment Group | Mouse Tail Bleeding Time (sec.) | % Increase |
|---|---|---|
| Control | 37.0 ± 5.25 | |
| Aspirin (100 mg/kg) | 72.88 ± 10.9 | 97 |
| Compound III (100 mg/kg) | 139.0 ± 22.51 | 276 |
| Compound VIII (100 mg/kg) | 139.88 ± 28.23 | 278 |

Statistical analysis by Student't test:
Compound III>aspirin, $P<0.02$
Compound VIII>aspirin, $P<0.05$ The above statistical analysis shows that both Compound III and Compound VIII are more potent than aspirin in the suppression of platelet aggregation. It is noted that the tendency of platelets to aggregate can contribute to the development or extension of clots and thus induce or worsen stroke or myocardial infarction.

Example 32. Effects of Edemas Provoked by Neutral Proteases

Both tryptic activity and collagenase activity are components of the tissue-injuring neutral proteinase activities secreted by neutrophils. Collagenase activity has also been associated with injury to cartilage; and, in another context, with the micro-injury to blood vessels that permits the extravasation and metastasis of, and by, tumor cells.

The effects of Compound III on rat and mouse paw edema as provoked by injection of these enzymes were evaluated. SOD injected IV and Compound III injected IP and IV at zero time, (as in Example 25), inhibited edema at two hours by from 33–40 percent, in both species. These data demonstrate that in the mouse 150 units of SOD are equipotent with 50 mg/kg of Compound III. Both drug effects were significant by t test, SOD at $P<0.05$ and Compound III at $P<0.01$.

Further, mouse paw edema was provoked by two levels of clostridial collagenase enzyme, in the supramaximal range (0.05 μg/ml and 0.15 μg/ml), and treated with one level of drug (Compound III; 100 mg/kg divided equally and administered IV and IP at zero time). The maximal drug inhibition observed was 81 percent at one hour and 87 percent at two hours, for the lower level of enzyme. Drug effects were significant by t test at both levels of enzyme and at both time points, at levels of $P<0.05$–$0.002$, except the group receiving the higher level of enzyme at two hours which was not significant.

Example 33: Inhibition of Ethanol-Induced Gastric Pathology by Compound III:Al

In an ethanol-induced pathology study similar to that of Example 19, pretreatment with 50 mg/kg of sucralfate one hour before ethanol inhibited all focal submucosal lesions (which derive from blood vessel damage and thrombosis). All large vessel vasodilation provoked by ethanol was also inhibited one hour after ethanol treatment. However, at three hours all therapeutic effects of sucralfate on ethanol-produced gastric pathology were absent.

On the other hand, in an identical study using Compound III:Al pretreatment with 50 mg/kg Compound III:Al inhibited all focal lesions provoked by ethanol after one hour without suppressing large-vessel vasodilation. At three hours after ethanol administration, this drug continued to suppress ethanol-induced focal lesions (−57 percent).

A suspension of 25 mg/kg sucralfate+25 mg/kg Compound III:Al in combination was given as a pretreatment administration to another group in the same study. The combination produced an unanticipated augmentation of therapeutic effect against ethanol-induced focal submucosal lesions (−90 percent) at three hours post-ethanol administration. The same interactive phenomenon was also observed when Compound III was used, rather than Compound III:Al.

Data for the above studies are shown below:

I. Focal Lesions per Stomach, One Hour Post-Ethanol (n = 6)

| Control | Sucralfate 50 mg/kg | Compound III:Al 50 mg/kg |
|---|---|---|
| 4.17 ± 1.58 | 0.00 (−100%) | 0.00 (−100%) |

Statistical analysis by Student's t test: the means of both treatment groups are significantly less than that of the Control, $p<0.05$.

II. Focal Lesions per Stomach, Three Hours Post-Ethanol (n = 17)

| Control | Sucralfate 50 mg/kg | Compound III:Al 50 mg/kg | Sucralfate, 25 mg/kg + Compound III:Al 25 mg/kg |
|---|---|---|---|
| 4.94 ± 1.41 | 5.24 ± 1.49 (+6%) | 2.12 ± 0.87 (−57%) | 0.47 ± 0.21 (−90%) |

Statistical analysis by Student's t test: Control v. Compound III:Al, $P<0.1$; Control v. Sucralfate + Compound III:Al, $P<0.005$.

III. Focal Lesions per Stomach, Three Hours Post-Ethanol. Study Employing Compound III

| Control | Sucralfate 50 mg/kg | Compound III:Al 50 mg/kg | Sucralfate, 25 mg/kg + Compound III 25 mg/kg |
|---|---|---|---|
| 2.25 ± 0.98 | 3.25 + 1.01 (+44%) | 1.50 + 0.76 (−33%) | 0.38 + 0.38 (−83%) |

Statistical analysis by Student's t test: Control v. Sucralfate, $P<0.02$; Control v. Compound III not significant.

Example 34: Effects of Compound III:Al on the Healing of Established Ulcers

To evaluate drug effects on peptic ulcer healing, gastric mucosal ulcers were produced in rats, after a two day fast, by a modification of the method of Konturek et al., *Am. J. Med.*, Vol. 86, 6A, 32 (1989). Briefly, to produce a mucosal ulcer, Konturek et al. applied 100 percent acetic acid for twenty seconds to the stomach serosa through a small cylindrical mold, 4.2 mm in diameter. The aim here was to make ulceration more severe than was achieved by the Konturek group so that spontaneous healing would not be as pronounced as they found in the controls, over an experimental period of seven days. Therefore, the mold was enlarged so that it had a diameter of 7.0 mm, and the period of acid-serosa contact was lengthened to 40 seconds.

All drugs studied were suspended in 0.25 percent (by weight) aqueous methylcellulose solution as the vehicle or diluent, which also served as the placebo given to the controls. Treatments were given once daily by oral gavage, in one milliliter of vehicle. The treatment groups were: Control; Sucralfate at 200 mg/kg; and Compound III:Al at 200 mg/kg.

At the end of the treatment period, stomachs were removed, ulcer diameters were measured, and determination was made of the presence or absence of perforation.

A. First Study

A first study was carried out to establish the ulcer state 24 hours after induction, just before the initiation of treatments. Data for this work are given below.

ESTABLISHED ULCERS AT 24 HOURS
(No Treatment)

Groups:
I. Control
SCORE = area of ulcer on Day 1 in $cm^2$, + 2.0 for the presence of ulcer perforation.

| Scores for Studied Animals |
|---|
| 0.35 |
| 0.25 |
| 0.35 |
| 0.35 |
| 0.35 |
| 0.25 |
| 0.35 |
| 0.35 |
| 0.70 |
| 0.45 |
| 0.56 |
| 0.12 |
| Mean Score 0.37 ± 0.04 |

A second study was carried out in which ulcer evolution was permitted to take place over five additional days, in the absence and presence of treatment with Sucralfate. The data are given below.

ESTABLISHED ULCER SCORES AFTER SIX DAYS
(Control and Treatment)

Groups:
I. Control
II. Sucralfate, 200 mg/kg
SCORE = area of ulcer on Day 6 in $cm^2$, + 2.0 for the presence of ulcer perforation.

Scores for Studied Animals

| | Group I | Group II |
|---|---|---|
| | 1.80 | 2.96* |
| | 4.1* | 5.75* |
| | 6.62* | 3.0* |
| | 1.44 | 1.0 |
| | 1.4 | 0.96 |
| | 5.75* | 3.5* |
| | 1.32 | 1.5 |
| | 4.3* | 0.1 |
| | 0.54 | 1.05 |
| | —* | 0.4 |
| MEAN SCORE | 3.03 ± 0.73 | 2.02 ± 0.55 |
| DRUG EFFECT | | −33% |

Statistical Analysis, by Student's t test: Group II < Group I, not significant.
*perforation Note that control ulcers get strikingly worse between day one and day six. In the sucralfate group a therapeutic trend is noted but the group n is not large enough to allow statistical significance to be reached.

A third study was begun one day following the start of study 2, in which ulcer evolution was allowed to take place over five additional days, in the absence and presence of treatment with Compound III:Al. The data are given below.

ESTABLISHED ULCER SCORES AFTER SIX DAYS
(Control and Treatment)

Groups:
I. Control
II. Compound III:Al, 200 mg/kg
SCORE = area of ulcer on Day 6 in $cm^2$, + 2.0 for the presence of ulcer perforation.

Scores for Studied Animals

| | Group I | Group II |
|---|---|---|
| | 3.44* | 1.2 |
| | 4.8* | 5.75* |
| | 3.8* | 0.72 |
| | 4.8* | 0.8 |
| | 9.5* | 0.5 |
| | 4.0* | 0.3 |
| | 2.8* | 0.56 |
| | 3.4* | 1.4 |
| | 3.0* | 0.90 |
| | 1.7 | 1.44 |
| MEAN SCORE | 4.12 ± 0.67 | 0.82 ± 0.13 |
| DRUG EFFECT | −80% | |

Statistical Analysis, by Student's t test: Group II < Group I, $P < 0.001$.
*perforation As before, the control ulcers became significantly worse between days one and six. Compound III:Al exerted a highly significant therapeutic effect. The data below show that a significant therapeutic effect remained for Compound III:Al even if the data concern only the calculated ulcer areas, without consideration of perforations.

ESTABLISHED ULCER AREAS IN $CM^2$, ON DAY SIX
(Control and Treatment)

| A. | | Control | Sucralfate |
|---|---|---|---|
| | MEAN | 2.14 ± 0.43 | 1.22 ± 0.31 |
| | | DRUG EFFECT | −43% |

Statistical analysis, by Student's t test: Control > Sucralfate, $P < 0.1$.

| B. | | Control | Compound III:Al |
|---|---|---|---|
| | MEAN | 2.32 ± 0.61 | 0.82 ± 0.13 |
| | | DRUG EFFECT | −65% |

Statistical analysis, by Student's t test: Control > Compound III:Al, $P < 0.05$.

B. Second Study

In another study, after ulcer induction as above, a different dosage protocol was employed at 24 hours to evaluate the interaction of Compound III and orally administered sucralfate on ulcer healing. It was previously observed that Compound III used alone did not enhance the healing process. Here, daily drug doses of the following were used: (a) sucralfate at 200 mg/kg, alone and (b) in combination with 80 mg/kg Compound III given by mouth at −45 minutes, and, in a third group, (c) in combination with 10 mg/kg Compound III given IV also at −45 minutes. In this interaction study, drug treatment was continued for three and not five days, as was the case for the above studies, followed by passage of two additional non-treatment days before sacrifice of animals for evaluation of stomach ulcer area and perforation. Data are given below.

| ESTABLISHED ULCER AREAS IN $CM^2$, ON DAY SIX (Comparative Treatments) | | | |
|---|---|---|---|
| | Sucralfate | Oral Compound III + Sucralfate | IV Compound III + Sucralfate |
| MEAN | 2.11 ± 0.41 | 0.72 ± 0.25 | 1.41 ± 0.42 |
| DRUG EFFECT | | −66% | |

Statistical Analysis, by Student's t test: Sucralfate < Oral Compound III + Sucralfate, P < 0.02. Sucralfate > IV Compound III + Sucralfate, P 0.1

These data illustrate that Compound III and Sucralfate effect an emergent enhancement of the healing of established gastric ulcers. Employing the control groups of the prior study, it is thought that conditions were created under which two drugs that fail to enhance ulcer-healing when used separately do so when used together.

C. Combined Study

Data from all ulcer-healing studies employing a drug dosage of 200 mg/kg and the same ulcerogenesis protocol were pooled as to the frequency of gastric perforation observed on day five, not shown separately, with the day six perforation data shown above. These combined data are presented below.

| Ulcer Perforation (Control and Treatments) | | |
|---|---|---|
| Group | Perforation Frequency | As Percent |
| Control | 26/52 | 50 |
| Sucralfate | 12/32 | 38 |
| Compound III:Al | 0/49 | 0 |

Statistical Analysis by Chi Square: Compound III:Al < Control, P < 0.001; Compound III:Al < Sucralfate, P < 0.001.

The small difference between Sucralfate and Control was not significant.

The foregoing is intended as illustrative of the present invention but not limiting- Numerous variations and modifications may be effected without departing from the true spirit and scope of the novel concepts of the invention.

What is claimed is:

1. An aldofuranose ring compound containing a carbon atom skeleton having 5-7 carbon atoms in which each of the 1- and 2-positions of said furanose ring has a substituent group that is electrically neutral at pH 7.2-7.6, the 1-position substituent group being hydroxyl, $C_1$-$C_6$ ester, $C_1$-$C_6$ alkyl ether, benzyl ether, $C_1$-$C_8$ alkyl or aryl urethane, and the 2-position substituent being hydrogen or a 1-position substituent group, or the 1- and 2-position substituent groups together forming an alkylidene bis-ether of the formula $CR^3R^4$ wherein $R^3$ and $R^4$ are independently hydrogen or $C_1$-$C_6$ alkyl with the total number of carbon atoms in $CR^3R^4$ being nine or fewer, or $CR^3R^4$ together form an unsubstituted cycloaliphatic group containing a total of 5-9 carbon atoms, and in which two to four of the remaining aldofuranose skeletal carbon atoms bear an oxygen-linked radical that is a sulfate ester, a phosphate ester or an ether-linked carbon-bonded carboxylate having an anionic charge at pH 7.2-7.6, the anionic charge of said radical being neutralized by a pharmaceutically acceptable cation.

2. The aldofuranose ring compound according to claim 1 wherein said carbon atom skeleton contains 6 carbon atoms.

3. The aldofuranose ring compound according to claim 1 wherein said 1- and 2-position substituent groups are ether-linked to said aldofuranose ring, with the non-aldofuranose portion of the ether groups containing a total of up to 9 carbon atoms.

4. The aldofuranose ring compound according to claim 1 wherein said oxygen-linked radical contains a sulfate, phosphate or carbon-bonded carboxylate group.

5. The aldofuranose ring compound according to claim 4 wherein said carbon-bonded carboxylate group of said oxygen-linked radical is linked to said oxygen atom through an alkylene or alkylidene group.

6. A compound of the chemical formula

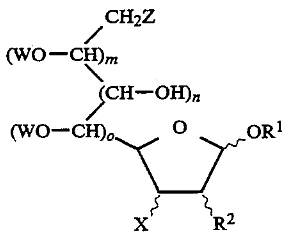

wherein $R^1$ is selected from the group consisting of hydrogen, $C_1$-$C_6$ alkyl, $C_1$-$C_6$ acyl, benzyl and $C_1$-$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5-9 carbon atoms in the ring;

OW is a radical that is selected from the group consisting of a sulfate ester, a phosphate ester and an ether-linked carbon-bonded carboxylate in which the anionic charge is neutralized by a pharmaceutically acceptable cation;

X is H, OH or OW;

Z is H, OH or OW;

at least two OW groups are present;

m is zero or 1;

n is zero or 1; and o is zero, 1 or 2; such that a) the sum of m+n+o is zero, 1 or 2, and b) m is zero when n is zero.

7. The compound according to claim 6 wherein the sum of m+n+o is 1.

8. The compound according to claim 7 wherein o is 1.

9. The compound according to claim 8 wherein $R^1$ and $R^5$ together form a $CR^3R^4$ group.

10. The compound according to claim 9 wherein o is zero.

11. The compound according to claim 10 wherein $R^1$ and $R^5$ together form a $CR^3R^4$ group.

12. The compound according to claim 6 wherein Z is OW.

13. The compound according to claim 12 wherein $R^1$ and $R^5$ together form a $CR^3R^4$ group.

14. The compound according to claim 13 wherein the sum of m+n+o is 1.

15. The compound according to claim 14 wherein o is 1.

16. The compound according to claim 14 wherein o is zero.

17. A glucofuranose or allofuranose substituted at the 3,5,6- or 3,6-positions by a radical that is a sulfate ester, a phosphate ester or an ether-linked carbon-bonded carboxylate and is anionic at pH 7.2–7.6, the anionic charge of said radical being neutralized by a pharmaceutically acceptable cation.

18. The glucofuranose or allofuranose of claim 17 wherein the 1- and 2-position oxygen atoms are etherified, with the non-glucofuranose or non-allofuranose portion of the ether groups being $C_1$–$C_6$ alkyl, benzyl, or together forming an alkylidene bis-ether of the formula $CR^3R^4$ wherein $R^3$ and $R^4$ are independently hydrogen or $C_1$–$C_6$ alkyl with the total number of carbon atoms in $CR^3R^4$ being nine or fewer, or $CR^3R^4$ together form an unsubstituted cycloaliphatic group containing a total of 5–9 carbon atoms.

19. The glucofuranose or allofuranose of claim 18 wherein the ether is an acetal or ketal.

20. The glucofuranose or allofuranose of claim 18 wherein the anionic radical is a sulfate, phosphate or carbon-bonded carboxylate radical.

21. A compound having a structural formula

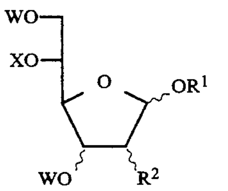

wherein W is selected from the group consisting of $SO_3M$, $PO_3M_2$ and $R^6CO_2M$ in which $R^6$ is $(CH_2)_n$, where n is 1–5;

X is H or W;

$R^1$ is H or $C_1$–$C_6$ alkyl;

$R^2$ is H or $R^5$ wherein $R^5$ is OH or O-$C_1$–$C_6$ alkyl, with the total number of carbon atoms in $R^1$ plus $R^5$ being 9 or fewer; or $R^1$ and $R^5$ together form a $CR^3R^4$ group in which (a) $R^3$ and $R^4$ are independently selected from H or $C_1$–$C_6$ alkyl with the total number of carbon atoms in $CR^3R^4$ being 1-9, or (b) $CR^3R^4$ together form an unsubstituted cycloaliphatic group containing a total of 5–9 carbon atoms in the ring; and M is a pharmaceutically acceptable cation.

22. The compound of claim 21 wherein W is $SO_3M$ and X is W.

23. The compound of claim 22 wherein $R^1$ and $R^5$ together form a $CR^3R^4$ group.

24. The compound of claim 23 wherein said $CR^3R^4$ group is selected from the group consisting of 2-propylidene, 3-pentylidene and 5-nonylidene.

25. The compound of claim 21 wherein W is $PO_3M_2$ and X is H.

26. The compound of claim 25 wherein $R^1$ and $R^5$ together form a $CR^3R^4$ group.

27. The compound of claim 21 wherein said pharmaceutically acceptable cation is aluminum that is present at about 25 percent to about 55 percent by weight of said compound.

28. 1,2-O-Propylidene )-3,5,6-tri-O-sulfo-α-D-allofuranose, tripotassium salt.

29. 3,5,6-Tri-O-sulfo-α-D-allofuranose, tripotassium salt.

30. A compound of the chemical formula

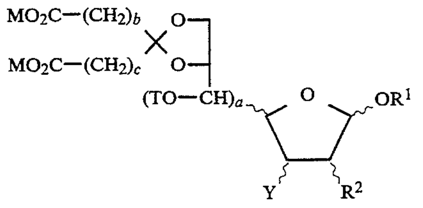

wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

Y is H, OH, $SO_3M$ or $PO_3M$;

T is H, $OSO_3M$ or $OPO_3M$, and when T is other than H and Y is other than H or OH, OT and Y are the same;

a is zero or 1;

b is zero, 1, 2 or 3;

c is zero, 1, 2 or 3, with the sum of b+c being no more than 5; and

M is a physiologically acceptable cation.

31. The compound according to claim 30 wherein $R^1$ and $R^5$ together form a $CR^3R^4$ group.

32. The compound according to claim 31 wherein Y is H and a is zero.

33. The compound according to claim 32 wherein b=c=1.

34. A pharmaceutical composition comprising a physiologically tolerable diluent and an anti-inflammatory effective amount of an aldofuranose ring compound whose carbon skeleton contains 5–7 carbon atoms, whose 1- and 2-positions have a substituent group that is electrically neutral at pH 7.2–7.6, the 1-position substituent group being hydroxyl, $C_1$–$C_6$ ester, $C_1$–$C_6$ alkyl ether, benzyl ether, $C_1$–$C_8$ alkyl or aryl urethane, and the 2-position substituent being hydrogen or a 1-position substituent group, or the 1- and 2-position substituent groups together forming an alkylidene bis-ether of the formula $CR^3R^4$ wherein $R^3$ and $R^4$ are independently hydrogen or $C_1$–$C_6$ alkyl with the total number of carbon atoms in $CR^3R^4$ being nine or fewer, or $CR^3R^4$ together form an unsubstituted cycloaliphatic group containing a total of 5–9 carbon atoms, and two through four of whose remaining skeletal ring carbons present having an oxygen-linked radical that is a sulfate ester, a phosphate ester or an ether-linked carbon-bonded carboxylate that bears an anionic charge at pH 7.2–7.6, which charge is neutralized by a pharmaceutically acceptable cation.

35. The pharmaceutical composition according to claim 34 wherein said aldofuranose ring compound corresponds to the chemical formula

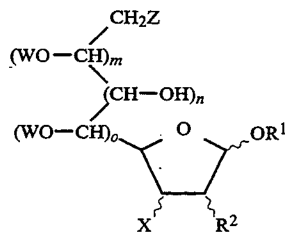

wherein $R^1$ is selected from the group consisting of hydrogen, $C_1$-$C_6$ alkyl, $C_1$-$C_6$ acyl, benzyl and $C_1$-$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

OW is a radical that is selected from the group consisting of a sulfate ester, a phosphate ester and an ether-linked carbon-bonded carboxylate in which the anionic charge is neutralized by a pharmaceutically acceptable cation;

X is H, OH or OW;

Z is H, OH or OW;

at least two OW groups are present;

m is zero or 1;

n is zero or; and o is zero, 1 or 2; such that a) the sum of m+n+o is zero, 1 or 2, and b) m is zero when n is zero.

36. The pharmaceutical composition according to claim 35 wherein Z is OW.

37. The pharmaceutical composition according to claim 34 wherein said aldofuranose ring compound corresponds to the chemical formula

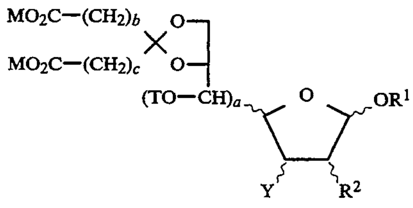

wherein $R^1$ is selected from the group consisting of hydrogen, $C_1$-$C_6$ alkyl, $C_1$-$C_6$ acyl, benzyl and $C_1$-$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$-$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

Y is H, OH, $OSO_3M$ or $OPO_3M$;

T is H, $SO_3M$ or $PO_3M$, and when T is other than is H and Y is other than H or OH, OT and Y are the same;

a is zero or 1;

b is zero, 1, 2 or 3;

c is zero, 1, 2 or 3, with the sum of b+c being no more than 5; and

M is a physiologically acceptable cation.

38. The pharmaceutical composition according to claim 34 wherein said aldofuranose ring compound corresponds to the chemical formula

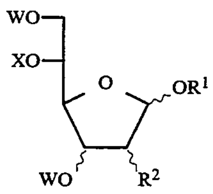

wherein W is selected from the group consisting of $SO_3M$, $PO_3M_2$ and $R^6CO_2M$ in which $R^6$ is $(CH_2)_n$, where n is 1–5;

X is H or W;

$R^1$ is H or $C_1$-$C_6$ alkyl;

$R^2$ is H or $R^5$ wherein $R^5$ is OH or O-$C_1$-$C_6$ alkyl; or $R^1$ and $R^5$ together form a $CR^3R^4$ group in which (a) $R^3$ and $R^4$ are independently selected from H or $C_1$-$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring; and M is a pharmaceutically acceptable cation.

39. The pharmaceutical composition according to claim 38 wherein said aldofuranose is a glucofuranose or allofuranose.

40. The pharmaceutical composition of claim 39 wherein the 1- and 2-position oxygen atoms of said glucofuranose or allofuranose are etherified as a ketal or acetal containing a total of up to 9 carbon atoms.

41. The pharmaceutical composition of claim 39 wherein said glucofuranose or allofuranose contains sulfo groups at the 3,5,6-positions.

42. A method of treating an inflammatory or gastric ulcerative condition in a mammal comprising administering to a mammal with an inflammatory or gastric ulcerative condition an anti-inflammatory effective amount of an aldofuranose ring compound whose carbon skeleton contains 5–7 carbon atoms, whose 1- and 2-positions have a substituent group that is electrically neutral at pH 7.2–7.6, the 1-position substituent group being hydroxyl, $C_1$-$C_8$ ester, $C_1$-$C_6$ alkyl ether, benzyl ether, $C_1$-$C_6$ or aryl urethane, and the 2-position substituent being hydrogen or a 1-position substituent group, or the 1- and 2-position substituent groups together forming an alkylidene bis-ether of the formula $CR^3R^4$ wherein $R^3$ and $R^4$ are independently hydrogen or $C_1$-$C_6$ alkyl with the total number of carbon atoms in $CR^3CR^4$ being nine or fewer or $CR^3R^4$ together form an unsubstituted cycloaliphatic group containing a total of 5–9 carbon atoms, and two through four of whose remaining skeletal ring carbons present having an oxygen-linked radical that is a sulfate ester, phosphate ester or an ether-linked carbon-bonded carboxylate that bears an anionic charge at pH 7.2–7.6, which charge is neutralized by a pharmaceutically acceptable cation.

43. The method according to claim 42 wherein said aldofuranose ring compound corresponds to the chemical formula

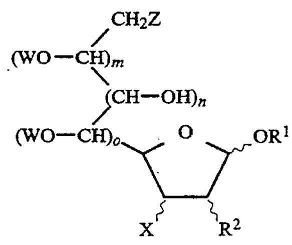

wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

OW is a radical that is selected from the group consisting of a sulfate ester, a phosphate ester and an ether-linked carbon-bonded carboxylate in which the anionic charge is neutralized by a pharmaceutically acceptable cation;

X is H, OH or OW;

Z is H, OH or OW;

at least two OW groups are present;

m is zero or 1;

n is zero or; and o is zero, 1 or 2; such that a) the sum of m+n+o is zero, 1 or 2, and b) m is zero when n is zero.

44. The method according to claim 43 wherein Z is OW.

45. The method according to claim 42 wherein said aldofuranose ring compound corresponds to the chemical formula

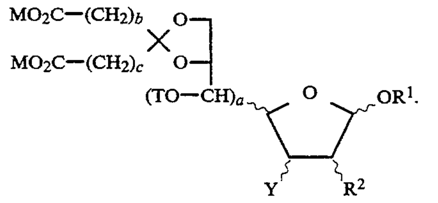

wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

Y is H, OH, $OSO_3M$ or $OPO_3M$;

T is H, $SO_3M$ or $PO_3M$, and when T is other than H and Y is other than H or OH, OT and Y are the same;

a is zero or 1;

b is zero, 1, 2 or 3;

c is zero, 1, 2 or 3, with the sum of b+c being no more than 5; and

M is a physiologically acceptable cation.

46. The method according to claim 42 wherein said aldofuranose ring compound corresponds to the chemical formula

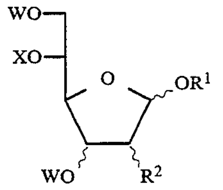

wherein W is selected from the group consisting of $SO_3M$, $PO_3M_2$ and $R^6CO_2M$ in which $R^6$ is $(CH_2)_n$, where n is 1–5;

X is H or W;

$R^1$ is H or $C_1$–$C_6$ alkyl;

$R^2$ is H or $R^5$ wherein $R^5$ is OH or O-$C_1$–$C_6$ alkyl; or $R^1$ and $R^5$ together form a $CR^3R^4$ group in which (a) $R^3$ and $R^4$ are independently selected from H or $C_1$–$C_6$ alkyl with the total number of carbon atoms in $CR^3R^4$being nine or fewer, or (b) $CR^3R^4$ together form an unsubstituted cycloaliphatic group containing a total of 5–9 carbon atoms in the ring; and M is a pharmaceutically acceptable cation.

47. The method according to claim 46 wherein said aldofuranose is a glucofuranose or allofuranose substituted at the 3,5,6- or 3,6-positions with said oxygen-linked radical.

48. The method of claim 42 wherein said inflammatory condition is edema.

49. The method of claim 42 wherein said inflammatory condition is gastric ulceration.

50. The method of claim 42 wherein said inflammatory condition is ischemia-induced.

51. A method of inhibiting neutrophil influx to a site of inflammation in a mammal comprising administering to a mammal having a site of inflammation a neutrophil-inhibiting effective amount of an aldofuranose ring compound whose carbon skeleton contains 5–7 carbon atoms, whose 1- and 2-positions have a substituent group that is electrically neutral at pH 7.2–7.6, the 1-position substituent group being hydroxyl, $C_1$–$C_6$ ester, $C_1$–$C_6$ alkyl ether, benzyl ether, $C_1$–$C_8$ alkyl or aryl urethane, and the 2-position substituent being hydrogen or a 1-position substituent group, or the 1- and 2-position substituent groups together forming an alkylidene bis-ether of the formula $CR^3R^4$ wherein $R^3$ and $R^4$ are independently hydrogen or $C_1$–$C_6$ alkyl with the total number of carbon atoms in $CR^3CR^4$ being nine or fewer, or $CR^3R^4$ together form an unsubstituted cycloaliphatic group containing a total of 5–9 carbon atoms, and two through four of whose remaining skeletal ring carbons present having an oxygen-linked radical that is a sulfate ester, a phosphate ester or an ether-linked carbon-bonded carboxylate that bears an anionic charge at pH 7.2–7.6, which charge is neutralized by a pharmaceutically acceptable cation.

52. The method according to claim 51 wherein said aldofuranose ring compound corresponds to the chemical formula

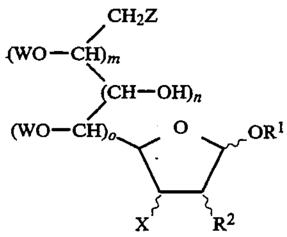

wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^3$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

OW is a radical that is selected from the group consisting of a sulfate ester, a phosphate ester and an ether-linked carbon-bonded carboxylate in which the anionic charge is neutralized by a pharmaceutically acceptable cation;

X is H, OH or OW;

at least two OW groups are present;

m is zero or 1;

n is zero or 1; and o is zero, 1 or 2; such that a) the sum of m+n+o is zero, 1 or 2, and b) when n is zero, m is zero.

53. The method according to claim 51 wherein said aldofuranose ring compound corresponds to the chemical formula

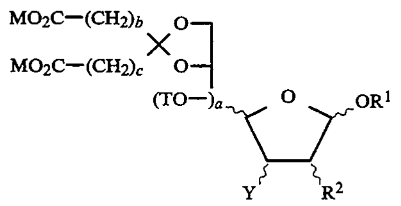

wherein $R^1$ is selected from the group consisting of hydrogen, $C_1$–$C_6$ alkyl, $C_1$–$C_6$ acyl, benzyl and $C_1$–$C_8$ carbamoyl;

$R^2$ is hydrogen or $R^5$ wherein $R^5$ is $OR^1$;

or $R^1$ and $R^5$ together form a $CR^3R^4$ group in which (a) $R^2$ and $R^4$ are independently hydrogen or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring;

Y is H, OH, $OSO_3M$ or $OPO_3M$;

T is H, $SO_3M$ or $PO_3M$, and when T is other than H and Y is other than H or OH, OT and Y are the same;

a is zero or 1;

b is zero, 1, 2 or 3;

C is zero, 1, 2 or 3, with the sum of b+c being no more than 5; and

M is a physiologically acceptable cation.

54. The method according to claim 51 wherein said aldofuranose ring compound corresponds to the chemical formula

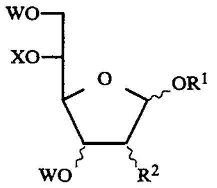

wherein W is selected from the group consisting of $SO_3M$, $PO_3M_2$ and $R^6CO_2M$ in which $R^6$ is $(CH_2)_n$, where n is 1–5;

X is H or W;

$R^1$ is H or $C_1$–$C_6$ alkyl;

$R^2$ is H or $R^5$ wherein $R^5$ is OH or O-$C_1$–$C_6$ alkyl; or $R^1$ and $R^5$ together form a $CR^3R^4$ group in which (a) $R^3$ and $R^4$ are independently selected from H or $C_1$–$C_6$ alkyl with the total number of carbon atoms in $CR^3R^4$ being nine or fewer, or (b) $CR^3R^4$ together form an unsubstituted cycloaliphatic group containing a total of 5–9 carbon atoms in the ring; and M is a pharmaceutically acceptable cation.

55. The method according to claim 54 wherein said aldofuranose is a glucofuranose or allofuranose substituted at the 3,5,6- or 3,6-positions with said oxygen-linked radical.

* * * * *